US010945981B2

(12) United States Patent
Gerner et al.

(10) Patent No.: US 10,945,981 B2
(45) Date of Patent: Mar. 16, 2021

(54) METHODS FOR TREATING FAMILIAL ADENOMATOUS POLYPOSIS

(71) Applicant: CANCER PREVENTION PHARMACEUTICALS, INC., Tucson, AZ (US)

(72) Inventors: Eugene Gerner, Tucson, AZ (US); Alfred Cohen, Tucson, AZ (US); Michelle Boytim, Tucson, AZ (US)

(73) Assignee: Cancer Prevention Pharmaceuticals, Inc., Tucson, AZ (US)

( * ) Notice: Subject to any disclaimer, the term of this patent is extended or adjusted under 35 U.S.C. 154(b) by 0 days.

(21) Appl. No.: 16/875,156

(22) Filed: May 15, 2020

(65) Prior Publication Data

US 2020/0360329 A1    Nov. 19, 2020

Related U.S. Application Data

(60) Provisional application No. 62/849,590, filed on May 17, 2019.

(51) Int. Cl.
| | | |
|---|---|---|
| *A61K 31/198* | (2006.01) | |
| *A61P 1/00* | (2006.01) | |
| *A61K 9/20* | (2006.01) | |
| *A61K 31/192* | (2006.01) | |

(52) U.S. Cl.
CPC .............. *A61K 31/198* (2013.01); *A61K 9/20* (2013.01); *A61K 31/192* (2013.01); *A61P 1/00* (2018.01)

(58) Field of Classification Search
CPC ...... A61K 31/198; A61K 9/20; A61K 31/192; A61P 1/00
USPC ....................................................... 514/564
See application file for complete search history.

(56) References Cited

U.S. PATENT DOCUMENTS

| | | |
|---|---|---|
| 4,309,442 A | 1/1982 | Bey |
| 4,330,559 A | 5/1982 | Bey et al. |
| 4,413,141 A | 11/1983 | Bey et al. |
| 4,499,072 A | 2/1985 | Sunkara |
| 4,859,452 A | 8/1989 | Ajani et al. |
| 4,925,835 A | 5/1990 | Heston |
| 5,002,879 A | 3/1991 | Bowlin |
| 5,814,625 A | 9/1998 | Larson et al. |
| 5,843,929 A | 12/1998 | Larson et al. |
| 6,258,845 B1 | 7/2001 | Gerner et al. |
| 6,573,290 B1 | 6/2003 | Love |
| 6,602,910 B2 | 8/2003 | Levenson |
| 6,753,422 B2 | 6/2004 | O'Brien et al. |
| 7,273,888 B2 | 9/2007 | Ramesh |
| 7,592,319 B2 | 9/2009 | Li et al. |
| 8,329,636 B2 | 12/2012 | Gerner et al. |
| 9,072,778 B2 | 7/2015 | Bachmann |
| 9,121,852 B2 | 9/2015 | Gerner et al. |
| 9,937,141 B2 | 4/2018 | Gerner et al. |
| 10,151,756 B2 | 12/2018 | Gerner et al. |
| 10,655,183 B2 | 5/2020 | Gerner et al. |
| 2002/0081611 A1 | 6/2002 | O'Brien |
| 2002/0110590 A1 | 8/2002 | Shaked et al. |
| 2005/0032726 A1 | 2/2005 | Li et al. |
| 2005/0059690 A1 | 3/2005 | Newman et al. |
| 2010/0197718 A1 | 8/2010 | Pisano et al. |
| 2010/0317708 A1 | 12/2010 | Gerner et al. |
| 2011/0256161 A1 | 10/2011 | Burns et al. |
| 2012/0259013 A1 | 10/2012 | Motwani et al. |
| 2013/0157972 A1 | 6/2013 | Cheng |
| 2013/0164751 A1 | 6/2013 | Gerner et al. |
| 2013/0216528 A1 | 8/2013 | Cheung et al. |
| 2013/0217743 A1 | 8/2013 | Raj et al. |
| 2015/0301060 A1 | 10/2015 | Gerner et al. |
| 2016/0213634 A1 | 7/2016 | Gerner et al. |
| 2017/0362658 A1 | 12/2017 | Gerner et al. |
| 2019/0113518 A1 | 4/2019 | Gerner et al. |
| 2020/0009098 A1 | 1/2020 | Shannon et al. |

FOREIGN PATENT DOCUMENTS

| | | |
|---|---|---|
| CA | 2 165 481 | 1/1995 |
| EP | 2 438 919 | 4/2012 |
| JP | 2002-509884 | 4/2002 |
| JP | 2012-511052 | 5/2012 |
| WO | WO 99/49859 | 10/1999 |
| WO | WO 01/68076 | 9/2001 |
| WO | WO 02/15895 | 2/2002 |
| WO | WO 2009/048932 | 4/2009 |
| WO | WO 2010/056919 | 5/2010 |
| WO | WO 2010/132817 | 11/2010 |
| WO | WO 2011/135459 | 11/2011 |
| WO | WO 2014/140072 | 9/2014 |

(Continued)

OTHER PUBLICATIONS

Kim et al Best Pract Res Clin Gastrointerol, 2011, 25(0) 607-622 (Year: 2011).*
"NCT01245816" dated Apr. 23, 2015, retrieved from clinicaltrials.gov archive on Jan. 20, 2017.
"NCT01483144" dated Jul. 28, 2015, retrieved from clinicaltrials.gov archive on Jan. 20, 2017.
"VANIQA®" (eflornithine hydrochloride) Prescription Information, dated Jul. 2010.
Alberts et al., "Do NSAIDs exert their colon cancer chemoprevention activities through the inhibition of mucosal prostaglandin synthetase?," *J. Cell. Biochem. Supp.*, (22):18-23, 1995.
Altman AM, Hui JYC, Tuttle TM, "Quality-of-life implications of risk-reducing cancer surgery," Br J Surg 2018;105:e121-e30.

(Continued)

*Primary Examiner* — Yevgeny Valenrod
(74) *Attorney, Agent, or Firm* — Parker Highlander PLLC

(57) ABSTRACT

Provided are methods for preventing or delaying the need for surgical intervention in a patient having familial adenomatous polyposis (FAP) and an at least partially intact lower gastrointestinal tract. Also provided are methods for preventing or delaying the formation of neoplasia and/or cancer in a patient having FAP. The methods comprise administering an effective amount of a pharmaceutical therapy that comprises eflornithine and sulindac to a patient having FAP and an intact lower gastrointestinal tract.

20 Claims, 10 Drawing Sheets

(56) References Cited

FOREIGN PATENT DOCUMENTS

| WO | WO 2016/130918 | 8/2016 |
|---|---|---|
| WO | WO 2017/075576 | 5/2017 |

OTHER PUBLICATIONS

Andrews L, Mireskandari S, Jessen J, et al., "Impact of familial adenomatous polyposis on young adults: quality of life outcomes. Dis Colon Rectum," 2007;50:1306-15.
Arber et al., "A K-ras oncogene increases resistance to sulindac-induces apoptosis in rat enterocytes," Gastroenterology, 113: 1892-1990, 1997.
Aretz S, Uhlhaas S, Caspari R, et al., "Frequency and parental origin of de novo APC mutations in familial adenomatous polyposis," Eur J Hum Genet 2004;12:52-8.
Babbar et al., "Induction of spermidine/spermine NL-acetyltransferase (SSAT) by aspirin in Caco-2 colon cancer cells," *Biochem. J.*, 394:317-24, 2006.
Bachrach et al., "Polyamines: new cues in cellular signal transduction," *News Physiol. Sci.*, 16:106-109, 2001.
Bailey et al., "A randomized, double-blind, placebo-controlled phase 3 skin cancer prevention study of {alpha}-difluoromethylornithine in subjects with previous history of skin cancer," *Cancer Prev Res (Phila)* 3, 35-47, 2010.
Barry et al., "Ornithine decarboxylase polymorphism modification of response to aspirin treatment for colorectal adenoma prevention," *J. Natl. Cancer Inst.*, 98(20):1494-500, 2006.
Basuroy and Gerner, "Emerging concepts in targeting the polyamine metabolic pathway in epithelial cancer chemoprevention and chemotherapy," *J. Biochem.*, 139(1):27-33, 2006.
Bedi et al., "Inhibition of apoptosis during development of colorectal cancer," *Cancer Res.*, 55(9):1811-1816, 1995.
Bello-Fernandez et al., "The ornithine decarboxylase gene is a transcriptional target of c-Myc," *Proc. Natl. Acad. Sci. USA*, 90:7804-8, 1993.
Bertagnolli MM, Eagle CJ, Zauber AG, et al., "Celecoxib for the Prevention of Sporadic Colorectal Adenomas," New Engl J Med 2006;355:873-84.
Boolbol et al., "Cyclooxygenase-2 overexpression and tumor formation are blocked by sulindac in a murine model of familial adenomatous polyposis," *Cancer Research*, 56:2556-2560, 1996.
Boone et al., "Biomarker end-points in cancer chemoprevention trails," IARC Scientific Publications, 142:273-280.
Boyle et al., "Polyamine contents in rectal and buccal mucosae in humans treated with oral difluoromethylornithine," *Cancer Epidemiol. Biomarkers Prev.*, 1:131-135, 1992.
Brabender et al., "Upregulation of ornithine decarboxylase mRNA expression in Barrett's esophagus and Barrett's-associated adenocarcinoma," *J. Gastrointest. Surg.*, 5:174-181; discussion 182, 2001.
Braverman et al., "Ornithine decarboxylase: an unreliable marker for the identification of population groups at risk for colonic neoplasia," Am. J. Gastronenterology, 85:723-726, 1990.
Bülow S, Björk J, Christensen IJ, et al., "Duodenal adenomatosis in familial adenomatous polyposis," Gut 2004;53:381-6.
Burke CA, Dekker E, Samadder NJ, Stoffel E, Cohen A., "Efficacy and safety of eflornithine (CPP-1X)/sulindac combination therapy versus each as monotherapy in patients with familial adenomatous polyposis (FAP): design and rationale of a randomized, double-blind, Phase III trial," BMC Gastroenterol 2016;16:87.
Burke CA, Phillips R, Berger M, et al. Children's International Polyposis (CHIP) study: a randomized, double-blind, placebo-controlled study of celecoxib in children with familial adenomatous polyposis Clin Exp Gastroenterol 2017;10:1-9.
Burn J, Bishop DT, Chapman PD, et al. A randomized placebo-controlled prevention trial of aspirin and/or resistant starch in young people with familial adenomatous polyposis. Cancer Prey Res (Phila) 2011;4:655-65.

Campos FG. Surgical treatment of familial adenomatous polyposis: dilemmas and current recommendations. World J Gastroenterol 2014;20:16620-9.
Castel et al., "Treatment of high-risk neuroblastoma with anti-GD2 antibodies," Clinical and Translational Oncology, 12:788-793, 2010.
Childs et al., "Polyamine-dependent gene expression," *Cell. Molec. Life Sci.*, 60:1394-1406, 2003.
Church, "Ileoanal pouch neoplasia in familial adenomatous polyposis: an underestimated threat," *Dis. Colon Rectum*, 48:1708-1713, 2005.
Croghan et al., "Dose-related alpha-difluoromethylornithine ototoxicity," Am. J. Clin. Oncol., (14):331-5, 1991.
Cruz-Correa M, Hylind LM, Romans KE, Booker SV, Giardiello FM, "Long-term treatment with sulindac in familial adenomatous polyposis: A prospective cohort study," Gastroenterology 2002;122:641-5.
Delker DA, Wood AC, Snow AK, et al., "Chemoprevention with Cyclooxygenase and Epidermal Growth Factor Receptor Inhibitors in Familial Adenomatous Polyposis Patients: mRNA Signatures of Duodenal Neoplasia," Cancer Prev Res (Phila) 2018;11:4-15.
Derynck et al., "TGF-beta signaling in tumor suppression and cancer progression," *Nature Genetics*, 29:117-29, 2001.
Dozois RR, Kelly KA, Welling DR, et al.,"Ileal pouch-anal anastomosis: comparison of results in familial adenomatous polyposis and chronic ulcerative colitis," Ann Surg.1989;210:268-71.
DuBois et al., "G1 delay in cells overexpressing prostaglandin endoperoxide synthase-2," *Cancer Res.*, 56:733-737, 1996.
Eisinger AL, Nadauld LD, Shelton DN, et al. The adenomatous polyposis coli tumor suppressor gene regulates expression of cyclooxygenase-2 by a mechanism that involves retinoic acid. J Biol Chem 2006;281:20474-82.
Erdman et al., "Assessment of Mutations in Ki-ras and P53 in colon cancers from azoxymethane-and dimethylhydrazine-treated rats," Mol. Carcin., (19):137-144, 1997.
Erdman et al., "APC-dependent changes in expression of genes influencing polyamine metabolism, and consequences for gastrointestinal carcinogenesis, in the Min mouse," *Carcinogenesis*, 20(9):1709-13, 1999.
Fearon et al., "A genetic model for colorectal tumorigenesis," *Cell*, 61:759-767, 1990.
Fultz and Gerner, "APC-dependent regulation of ornithine decarboxylase in human colon tumor cells," *Mol. Carcinog.*, 34:10-8, 2002.
Gamble et al., "Polyamine pathway inhibition as a novel therapeutic approach to treating neuroblastoma," Frontier in Oncology, 2(162):1-10, 2012.
Gann et al., "Low-dose aspirin and incidence of colorectal tumors in a randomized trial," *J. Natl. Cancer Inst.*, 85:1220-1224, 1993.
Gerner and Meyskens, "Polyamines and cancer: old molecules, new understanding," *Nature Rev. Cancer*, 4:781-92, 2004.
Gerner et al., Cancer pharmacoprevention: Targeting polyamine metabolism to manage risk factors for colon cancer. J. Biol. Chem., 293:18770-18778, 2018.
Gerner et al., "Combination chemoprevention for colon cancer targeting polyamine synthesis and inflammation," *Clinical Cancer Research*, 15(3):758-761, 2009.
Gerner et al., "Gastrointestinal tissue polyamine contents of patients with Barrett's esophagus treated with alpha-difluoromethylornithine," *Cancer Epidemiol. Biomarkers Prev.*, 3:325-330, 1994.
Gerner, "Impact of dietary amino acids and polyamines on intestinal carcinogenesis and chemoprevention in mouse models," *Biochemical Society Transactions*, 35(2):322-325, 2007.
Gerner, E. W., et al, "Rationale for, and design of, a clinical trial targeting polyamine metabolism for colon cancer chemoprevention." *Amino acids* 33.2 (2007): 189-195.
Giardiello et al., "Ornithine decarboxylase and polyamines in familial adenomatous polyposis," *Cancer Res.*, (57):199-201, 1997.
Greenberg et al., "Reduced risk of large-bowel adenomas among aspirin users," *J. Natl. Cancer Inst.*, 85:912-916, 1993.
Groves et al., "Prevalence and morphology of pouch and ileal adenomas in familial adenomatous polyposis" *Dis. Colon Rectum*, 48:816-823, 2005.
Guo et al., "Functional analysis of human ornithine decarboxylase alleles," *Cancer Res.*, 60(22):6314-6317, 2000.

(56) References Cited

OTHER PUBLICATIONS

Hanif et al., "Effects of nonsteroidal anti-inflammatory drugs on proliferation and on induction of apoptosis in colon cancer by a prostaglandin-independent pathway," *Biochemical Pharmacology*, (52):237-245, 1996.

Hessels et al., "Microbial flora in the gastrointestinal tract abolishes cytostatic effects of α-difluoromethylornithine in vivo," *Int. J. Cancer*, 43: 1155-1164, 1989.

Hixson et al., "Ornithine decarboxylase and polyamines in colorectal neoplasia and mucosa," *Cancer Epidemiology Biomarkers Prev.*, 2:369-374, 1993.

Hixson et al., "Sources of variability in measurements of ornithine decarboxylase activity and polyamine contents in colorectal mucosa," *Cancer Epidemoil. Biomarkers Prev.*, 3:317-323, 1994.

Hogarty et al., "ODC1 is a critical determinant of MYCN oncogenesis and a therapeutic target in neuroblastoma," *Cancer Res.*, 68:9735-9745, 2008.

Hubner et al., "Ornithine decarboxylase G316A genotype is prognostic for colorectal adenoma recurrence and predicts efficacy of aspirin chemoprevention," *Clin. Cancer Res.*, 14(8):2303-9, 2008.

Hughes, et al., "Polyamines reverse non-steroidal anti-inflammatory drug-induced toxicity in human colorectal cancer cells", Biochem J, 374:481-8, 2003.

Ignatenko et al., "Dietary putrescine reduces the intestinal anticarcinogenic activity of sulindac in a murine model of familial adenomatous polyposis," *Nutrition and Cancer*, 56(2): 172-181, 2006.

Ignatenko et al., "Role of c-Myc in intestinal tumorigenesis of the ApcMin/+ mouse," *Cancer Biol. Ther.*, 5(12):1658-64, 2006.

Iwamoto et al., "Expression of beta-catenin and full-length APC protein in normal and neoplastic colonic tissues," *Carcinogenesis*, 21:1935-40, 2000.

Jasperson KW, Tuohy TM, Neklason DW, Burt RW., "Hereditary and familial colon cancer Gastroenterology," 2010;138:2044-58.

Jass et al., "Emerging concepts in colorectal neoplasia," *Gastroenterology*, 123:862-876, 2002.

Johnson et al. "Relationships between drug activity in NCI preclinical in vitro and in vivo models and early clinical trials." *British Journal of Cancer* 84.10 (2001): 1424.

Kawamori et al., "Chemopreventive activity of celecoxib, a specific cyclooxygenase-2 inhibitor, against colon carcinogenesis," *Cancer Research*, 58:409-412, 1998.

Keller JJ, Giardiello FM. "Chemoprevetion strategies using NSAIDs and COX-2 inhibitors," Cancer Biol Ther 2003;2:S140-S9.

Kelloff et al., "Chemopreventive drug development: perspectives and progress," *Cancer Epidemiology Biomarks and Prevention*, 3:85-98, 1994.

Kelloff et al., "New agents for cancer chemoprevention," *J. Cell. Biochem.*, 265:1-28, 1996.

Kelloff et al., "Perspectives on chemoprevention agent selection and short term clinical prevention trials," *European J. Cancer Prevention*, 5(Supp. 2):79-85, 1996.

Kennedy RD, Potter DD, Moir CR, El-Youssef M. The natural history of familial adenomatous polyposis syndrome: a 24 year review of a single center experience in screening, diagnosis, and outcomes. J Pediatr Surg 2014;49:82-6.

Kingsnorth et al., "Effects of alpha-difluoromethylornithine and 5-fluorouracil on the proliferation of a human colon adenocarcinoma cell line," *Cancer Res.*, 43(9):4035-8, 1983.

Kruh et al., "Expression Pattern of MRP in Human Tissues and Adult Solid Tumor Cell Lines," *J. Natl. Cancer Inst.*, 87(16):1256-1258, 1995.

Ladenheim et al., "Effect of sulindac on sporadic colonic polyps," *Gastroenterology*, 108:1083-1087, 1995.

Lanza et al., "Peptic ulcer and gastrointestinal hemorrhage associated with nonsteroidal anti-inflammatory drug use in patients younger than 65 years. A large health maintenance organization cohort study," *Arch. Intern. Med.*, 155:1371-1377, 1995.

Latchford AR, Neale KF, Spigelman AD, Phillips RK, Clark SK., "Features of duodenal cancer in patients with familial adenomatous polyposis," Clin Gastroenterol Hepatol 2009;7:659-63.

Le et al., "Effects of socioeconomic status and treatment disparities in colorectal cancer survival," *Cancer Epidemiol. Biomarkers Prev.*, 17:1950-62, 2008.

Leonard D, Wolthuis A, D'Hoore A, et al. Different surgical strategies in the treatment of familial adenomatous polyposis: what's the role of the ileal pouch-anal anastomosis? Acta Gastroenterol Belg 2011;74:427-34.

Levin et al., "Relationship between ornithine decarboxylase levels in anaplastic gliomas and pregression-free survival in patients treated with DFMO-PCV chemotherapy," *International Journal of Cancer*, 121:(10): 2279-2283, 2010.

Linsalata et al., "Nutritional factors and polyamine metabolism in colorectal cancer," *Nutrition*, 24:382-389, 2008.

Lipkin, "New rodent models for studies of chemopreventive agents," *J. Cell Biochem. Suppl.*, 28-29:144-7, 1997.

Lippman, The dilemma and promise of cancer chemoprevention. *Nat. Clin. Pract. Oncol.*, 3(10):523, 2006.

Love et al., "Randomized phase I chemoprevention dose-seeking study of alpha-difluoromethylornithine," *J. Natl. Cancer Inst.*, 85:732-7, 1993.

Lozier et al., "Targeting ornithine decarboxylase reverses the LIN28/Let-7 axis and inhibits glycolytic metabolism in neuroblastoma," Oncotarget, 6:196-206, 2015.

Luk and Baylin, "Ornithine decarboxylase as a biologic marker in familial colonic polyposis," *N. Engl. J. Med.*, 311(2):80-83, 1984.

Lupulescu, "Control of precancer cell transformation into cancer cells: its relevance to cancer prevention," *Cancer Detect. Prev.*, 20(6):634-637, 1996.

Lynch PM, Burke CA, Phillips R, et al., "An international randomised trial of celecoxib versus celecoxib plus difluoromethylornithine in patients with familial adenomatous polyposis," Gut 2016;65:286-95.

Lynch PM, Morris JS, Wen S, et al., "A proposed staging system and stage-specific interventions for familial adenomatous polyposis," Gastrointest Endosc 2016;84:115-25 e4.

Mackenzie, Gerardo G., et al. "Phospho-sulindac (OXT-328) combined with difluoromethylornithine prevents colon cancer in mice." Cancer prevention research 4.7 (2011): 1052-1060.

Mallinckrodt Pharmaceuticals, Press Release May 19, 2019, Cancer Prevention Pharmaceuticals (CPP) and Mallinckrodt Announce Results from Pivotal Phase 3 Trial of CPP-1X/Sulindac in Patients with Familial Adenomatous Polyposis.

Martinez et al., "Pronounced reduction in adenoma recurrence associated with aspirin use and a polymorphism in the ornithine decarboxylase gene," *Proc. Natl. Acad. Sci. USA*, 100:7859-64, 2003.

Mathus-Vliegen EM, Boparai KS, Dekker E, van Geloven N. Progression of duodenal adenomatosis in familial adenomatous polyposis: due to ageing of subjects and advances in technology. Fam Cancer 2011;10:491-9.

Matsubara et al., "Association between high levels of ornithine decarboxylase activity and favorable prognosis in human colorectal carcinoma," *Clinical Cancer Res.*, 1:665-71, 1995.

McGarrity et al., "Colonic polyamine content and ornithine decarboxylase activity as markers for adenomas," *Cancer*, 66:1539-1543, 1990.

McLaren et al., "Longitudinal assessment of air conduction audiograms in a phase III clinical trial of difluoromethylornithine and sulindac for prevention of sporadic colorectal adenomas," *Cancer Prev. Res.*, 1(7):514-21, 2008.

Meyskens and Gerner, "Development of difluoromethylornithine as a chemoprevention agent for the management of colon cancer," *J. Cell. Biochem.*, 22:126-131, 1995.

Meyskens et al., "Development of difluoromethylornithine (DFMO) as a chemoprevention agent," *Clin. Cancer Res.*, 5:945-951, 1999.

Meyskens et al., "Difluoromethylornithine plus sulindac for the prevention of sporadic colorectal adenomas: a randomized placebo-controlled, double-blind trial," *Cancer Prev. Res.*, 1(1):32-8, 2008.

(56) References Cited

OTHER PUBLICATIONS

Meyskens et al., "Dose de-escalation chemoprevention trial of alpha-difluoromethylornithine in patients with colon polyps," *J. Natl. Cancer Inst.*, 86(15):1122-1130, 1994.

Meyskens et al., "Effect of alpha-difluoromethylornithine on rectal mucosal levels of polyamines in a randomized, double-blinded trial for colon cancer prevention," *J. Natl. Cancer Inst.*, 90(16):1212-8, 1998.

Muscat et al., "Nonsteroidal antiinflammatory drugs and colorectal cancer," *Cancer*, 74:1847-1854, 1994.

Narisawa et al., Inhibition of Development of Methylnitrosourea-induced Rat Colon Tumors by Indomethacin Treatment. *Cancer Res.*, 41(5):1954-1957, 1981.

Nishimura et al., "Independent roles of eIF5A and polyamines in cell proliferation," Biochem. J., 385:779-785, 2005.

O'Brien et al., "Differences in ornithine decarboxylase and androgen receptor allele frequencies among ethnic groups," *Molec. Carcinog.*, 41(2):120-3, 2004.

Parc YR, Olschwang S, Desaint B, Schmitt G, Parc RG, Tiret E.,"Familial adenomatous polyposis: prevalence of adenomas in the ileal pouch after restorative proctocolectomy," Ann Surg 2001;233:360-4.

Pardali and Moustakas, "Actions of TGF-beta as tumor suppressor and pro-metastatic factor in human cancer," *Biochimica et Biophysica Acta*, 1775:21-62, 2007.

Pasricha et al., "The effects of sulindac on colorectal proliferation and apoptosis in familial adenomatous polyposis," *Gastroenterology*, 109:994-998, 1995.

Paz et al., "Polyamines are oncometabolites that regulate the LIN28/let-7 pathway in colorectal cancer cells," Molecular Carcinogensis, 2013.

Peel et al., "Characterization of hereditary nonpolyposis colorectal cancer families from a population-based series of cases," *J. Natl. Cancer Inst.*, 92:1517-22, 2000.

Pegg, "Recent advances in the biochemistry of polyamines in eukaryotes," *Biochem.*, 234(2):249-262, 1986.

Piazza et al., "Antineoplastic drugs sulindac sulfide and sulfone inhibit cell growth by inducing apoptosis," *Cancer Res.*, (55):3110-3116, 1995.

Piazza et al., "Apoptosis primarily accounts for the growth-inhibitory properties of sulindac metabolites and involves a mechanism that is independent of cyclooxygenase inhibition, cell cycle arrest, and p53 induction," *Cancer Res.*, (57):2452-2459, 1989.

Piazza et al., "Sulindac sulfone inhibits azoxymethane-induced colon carcinogenesis in rats without reducing prostaglandin levels," *Cancer Res.*, (57):2909-2915, 1997b.

Pollard and Luckert, "Prevention and treatment of primary intestinal tumors in rats by piroxicam," *Cancer Res.*, 49:6471-6473, 1989.

Porter et al., "Polyamine biosynthetic activity in normal and neoplastic human colorectal tissue," *Cancer*, 60:1275-1281, 1987.

Quemener et al., "Polyamine deprivation: a new tool in cancer treatment," *Institute of Anticancer Research*, 14:443-448, 1994.

Raj et al., "Role of dietary polyamines in a phase III clinical trial of difluoromethylornithine (DFMO) and sulindac for prevention of sporadic colorectal adenomas," *British Journal of Cancer*, 108(3):512-518, 2013.

Rao et al., "Chemoprevention of colon carcinogenesis by sulindac, a nonsteroidal anti-inflammatory agent," *Cancer Res.*, (55):1464-1472, 1995.

Reddy et al., "Chemoprevention of colon carcinogenesis by concurrent administration of piroxicam, a nonsteroidal antiinflammatory drug with D,L-alpha-difluoromethylornithine, an ornithine decarboxylase inhibitor, in diet," *Cancer Research*, 50:2562-2568, 1990.

Reddy et al., "Dose-related inhibition of colon carcinogenesis by dietary piroxicam, a nonsteroidal antiinflammatory drug, during different stages of rat colon tumor development," *Cancer Res.*, 47:5340-5346, 1987.

Rial, Nathaniel S., Frank L. Meyskens, and Eugene W. Gerner. "Polyamines as mediators of APC-dependent intestinal carcinogenesis and cancer chemoprevention." Essays in biochemistry 46 (2009): 111-124.

Roberts and Wakefield, "The two faces of transforming growth factor beta in carcinogenesis," *Proc. Natl. Acad. Sci. USA*, 100:8621-3, 2003.

Roos VH, Bastiaansen BAJ, Dekker E., "Challenges and pitfalls of investigating duodenal cancer in patients with familial adenomatous polyposis," Gastrointest Endosc 2019;89:355-6.

Rounbehler et al., "Targeting ornithine decarboxylase impairs development of MYCN-amplified neuroblastoma," Cancer Res., 69:547-553, 2009.

Saletta et al., "Molecular profiling of childhood cancer: Biomarkers and novel therapies," BBA Clinical, 1:59-77, 2014.

Samadder NJ, Neklason DW, Boucher KM, et al. Effect of Sulindac and Erlotinib vs Placebo on Duodenal Neoplasia in Familial Adenomatous Polyposis: A Randomized Clinical Trial. JAMA 2016;315:1266-75.

Sainaha, Hanan S.; et al. "Modulanori of apoptosis by sulindac, curcumin, phenylethyl-3-methylcaffeate, and 6-phenylhexyl isothiocyanate: apoptotic index as a biomarker in colon cancer chemoprevention and promotion." *Cancer research* 57.7 (1997): 1301-1305.

Samal et al., "AMXT-1501, a novel polyamine transport inhibitor, synergizes with DFMO in inhibiting neuroblastoma cell proliferation by targeting both ornithine decarboxylase and polyamine transport," Int. J. Cancer, 133:1323-1334, 2013.

Saurin JC, Gutknecht C, Napoleon B, et al. Surveillance of duodenal adenomas in familial adenomatous polyposis reveals high cumulative risk of advanced disease. J Clin Oncol 2004;22:493-8.

Sausville, Edward A., and Angelika M. Burger. "Contributions of human tumor xenografts to anticancer drug development." Cancer Research 66.7 (2006): 3351-3354.

Seiler and Knodgen, "High-performance liquid chromatographic procedure for the simultaneous determination of the natural polyamines and their monoacetyl derivatives," *J. Chromatogr.*, 221(2):227-235, 1980.

Seiler et al., "Endogenous and exogenous polyamines in support of tumor growth," *Cancer Research*, 50:5077-5083, 1990.

Septer S, Lawson CE, Anant S, Attard T., "Familial adenomatous polyposis in pediatrics: natural history, emerging surveillance and management protocols, chemopreventive strategies, and areas of ongoing debate," Fam Cancer 2016;15:477-85.

Serrano PE, Grant RC, Berk TC, et al., "Progression and Management of Duodenal Neoplasia in Familial Adenomatous Polyposis: A Cohort Study," Ann Surg 2015;261:1138-44.

Sholler et al., [abstract]. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr LB-179. doi: 10.1158/1538-7445.

Silva et al., "Role of peripheral polyamines in the development of inflammatory pain," Biochemical Pharmacology, 82:269-277, 2011.

Simoneau et al., "Alpha-difluoromethylornithine and polyamine levels in the human prostate: results of a phase IIa trial," *J. Natl. Cancer Inst.*, 93:57-9, 2001.

Simoneau et al., "The effect of difluoromethylornithine on decreasing prostate size and polyamines in men: results of a year-long phase IIb randomized placebo-controlled chemoprevention trial," *Cancer Epidemiol. Biomarkers Prev.*, 17:292-9, 2008.

Singh and Reddy, "Molecular markers in chemoprevention of colon cancer. Inhibition of expression of ras-p21 and p53 by sulindac during azoxymethane-induced colon carcinogenesis," *Annals. NY Acad. Sci.*, (768):205-209, 1995.

Singh et al., "Bifidobacterium longum, a lactic acid-producing intestinal bacterium inhibits colon cancer and modulates the intermediate biomarkers of colon carcinogenesis," *Carcinogenesis*, 18:833-841, 1997.

Singh et al., "Modulation of azoxymethane-induced mutational activation of ras protooncogenes by chemopreventive agents in colon carcinogenesis," *Carcinogenesis*, (15):1317-1323, 1994.

(56) References Cited

OTHER PUBLICATIONS

Smithson et al., "Discovery of potent and selective inhibitors of Trypanosoma brucei ornithine decarboxylase," *The Journal of Biological Chemistry*, 265(22):16771-16781, 2010.

Soda et al., "Polyamine-rich food decreases age-associated pathology and mortality in aged mice," *Experimental Gerontology*, 44: 727-732, 2009.

Sourrouille I, Lefevre JH, Shields C, et al., "Surveillance of Duodenal Polyposis in Familial Adenomatous Polyposis: Should the Spigelman Score Be Modified?" Dis Colon Rectum 2017;60:1137-46.

Sporn & Hong, "Clinical Prevention of Recurrence of Colorectal Adenomas by the Combination of Difluoromethylornithine and Sulindac: An Important Milestone," Canc. Prev. Res., 1:9-11, 2008.

Spigelman et al., "Upper gastrointestinal cancer in patients with familial adenomatous polyposis," *Lancet*, 2:783-785, 1989.

Steinbach G, Lynch PM, Phillips RK, et al. The effect of celecoxib, a cyclooxygenase-2 inhibitor, in familial adenomatous polyposis. N Engl J Med 2000;342:1946-52.

Su et al., "Multiple intestinal neoplasia caused by a mutation in the murine homolog of the APC gene," *Science*, (256):668-670, 1992.

Syngal S, Brand RE, Church JM, et al., "ACG clinical guideline: Genetic testing and management of hereditary gastrointestinal cancer syndromes," Am J Gastroenterol 2015;110:223-62.

Tabib et al., "Role of polyamines in mediating malignant transformation and oncogene expression," *Int. J. Biochem. Cell. Biol.*, 31:1289-1295, 1999.

Tajika et al., "Prevalence of adenomas and carcinomas in the ileal pouch after proctocolectomy in patients with familial adenomatous polyposis," *J. Gastrointest. Surg.*, 13:1266-1273, 2009.

Tempero et al.,"Chemoprevention of mouse colon tumors with difluoromethylornithine during and after carcinogen treatment," *Cancer Res.*, 49(21):5793-7, 1989.

Thiruvengadam SS, Lopez R, O'Malley M, et al., "Spigelman stage IV duodenal polyposis does not precede most duodenal cancer cases in patients with familial adenomatous polyposis," Gastrointest Endosc 2019;89:345-54 e2.

Thomas and Thomas, "Polyamine metabolism and cancer," *J. Cell Mol. Med.*, 7:113-26, 2003.

Thompson et al., "Inhibition of mammary carcinogenesis by sulfone metabolite of sulindac," *J. Natl. Cancer Inst.*, (87):125-1260, 1995.

Thompson et al., "Levels of rectal mucosal polyamines and prostaglandin E2 predict ability of DFMO and sulindac to prevent colorectal adenoma," *Gastroenterology*, 139(3): 797-805, 2010.

Thompson, et al., "Sulfone metabolite of sulindac inhibits mammary carcinogenesis," Cancer Research, 57:267-271, 1997.

Thompson-Fawcett MW, Marcus VA, Redston M, Cohen Z, McLeod RS., "Adenomatous polyps develop commonly in the ileal pouch of patients with familial adenomatous polyposis," Dis Colon Rectum 2001;44:347-53.

Vander Heiden, M.G., "Targeting cancer metabolism: a therapeutic window opens, *Nat Rev Drug Discov* 10, 671-84, 2011.

Vane and Botting, "Mechanism of action of anti-inflammatory drugs," *Scand. J. Rheumatol.*, 25(Suppl. 102):9-21, 1996.

Visvanathan et al., "Association among an ornithine decarboxylase polymorphism, androgen receptor gene (CAG) repeat length and prostate cancer risk," *J. Urol.*, 171(2 Pt 1):652-5, 2004.

Wallace and Caslake, "Polyamines and colon cancer," *Eur J Gastroenterol Helatol.*, 13(9): 1033-1039, 2001.

Wallace, "The physiological role of the polyamines," *Eur. J. Clin. Invest.*, 30:1-3, 2000.

Wang et al., "Mucosal polyamine measurements and colorectal cancer risk," *J. Cell. Biochem.*, 63:252-257, 1996.

Wu JS, McGannon EA, Church JM., "Incidence of neoplastic polyps in the ileal pouch of patients with familial adenomatous polyposis after restorative proctocolectomy," Dis Colon Rectum 1998;41:552-6.

Zell et al., "Associations of a polymorphism in the ornithine decarboxylase gene with colorectal cancer survival," *Clin. Cancer Res.*, 15(19):6208-16, 2009.

Zell et al., "*Ornithine decarboxylase (Odc)*-1 gene polymorphism effects on baseline tissue polyamine levels and adenoma recurrence in a randomized phase III adenoma prevention trial of DFMO + sulindac versus placebo," *J. Clin. Oncol.*, 26(15S):Abstract 1502, 2008.

Zell et al., "Ornithine decarboxylase-1 polymorphism, chemoprevention with eflornithine and sulindac, and outcomes among colorectal adenoma patients," *J. Natl. Cancer Inst.*, 102(19):1513-1516, 2010.

Zell et al., "Risk and risk reduction involving arginine intake and meat consumption in colorectal tumorigenesis and survival," *Intl. J. Cancer*, 120:459-68, 2007.

Zell et al., "Risk of cardiovascular events in a randomized placebo-controlled, double-blind trial of difluoromethylornithine plus sulindac for the prevention of sporadic colorectal adenomas," *Cancer Prev. Res.*, 2(3):209-12, 2009.

Zell et al., "Survival after colorectal cancer diagnosis is associated with colorectal cancer family history," *Cancer Epidemiol. Biomarkers Prev.*, 17:3134-40, 2008.

Zeng, G. X., et al. "New concept and clinical application of colorectal intraepithelial neoplasia and carcinoma." Zhonghua wai ke za zhi [Chinese journal of surgery] 45.7 (2007): 449-451.

Ziogas and Anton-Culver, "Validation of family history data in cancer family registries," *Am. J. Prev. Med.*, 24:190-8, 2003.

Zoumas-Morse et al., "Development of a polyamine database for assessing dietary intake," *J. Am. Diet. Assoc.*, 107:1024-1027, 2007.

* cited by examiner

METHODS FOR TREATING FAMILIAL ADENOMATOUS POLYPOSIS

REFERENCE TO RELATED APPLICATIONS

The present application claims the priority benefit of U.S. provisional application No. 62/849,590, filed May 17, 2019, the entire contents of which is incorporated herein by reference.

BACKGROUND

1. Field

The present invention relates generally to the fields of cancer biology and medicine. More particularly, it concerns methods for treating patients having familial adenomatous polyposis.

2. Description of Related Art

Familial Adenomatous Polyposis (FAP) is a syndrome caused by mutations in the Adenomatous Polyposis Coli (APC) tumor suppressor gene and propagated by an autosomal dominant mode of inheritance. FAP is caused by mutations/deletions in the APC gene, which is located on chromosome 5q21-q22. Most FAP patients will have hundreds to thousands of colorectal adenomas, and without prophylactic surgery develop colorectal cancer before the age of 40. Prophylactic surgery may involve total abdominal colectomy with ileal-rectal anastomoses (IRA), accompanied by frequent rectal surveillance with polypectomy and cautery/laser ablation as needed. Patients with extensive rectal involvement undergo total proctocolectomy with ileal pouch-anal reconstruction.

Despite removing the main at-risk organ, many patients develop duodenal neoplasia (bulky adenomas/cancer) and require additional localized or Whipple radical surgery. The Spigelman classification (Stage 3 or 4) (Spigelman et al., 1989) can accurately predict those with adenomas that are most likely to progress to cancer. Bulow and colleagues (Bulow, 2004) reviewed duodenal polyposis issues in FAP patients. Gastric antral adenomas may occur and rarely are symptomatic or progress to cancer.

Despite total proctocolectomy with ileal pouch reconstruction, approximately 50% of patients will develop adenomatous lesions in the neo-rectum (Wu et al., 1998; Church, 2005; Tajika et al., 2009; Groves et al., 2005). There are case reports of cancer developing in the pouches. All patients who have a residual rectum after total colectomy require frequent surveillance, polypectomies and ablations for continuing rectal polyposis. As such, methods of controlling FAP progression in order to delay and/or prevent the occurrence of clinically meaningful events are needed.

SUMMARY

As such, in one aspect, provided herein are methods of treating a patient having familial adenomatous polyposis (FAP), the methods comprising administering to the patient a pharmaceutical therapy comprising a combined effective amount of eflornithine and sulindac, wherein the patient has an intact lower gastrointestinal tract or an at least partially intact lower gastrointestinal tract. In certain embodiments, a patient having an intact lower gastrointestinal tract has a colon, a rectum, and an ileal pouch. In certain embodiments, a patient having an at least partially intact lower gastrointestinal tract has a colorectum, a retained rectum, or an ileal pouch.

In one aspect, provide are methods of delaying or preventing a familial adenomatous polyposis (FAP) event and/or FAP progression in a patient with FAP, the method comprising administering to the patient a pharmaceutical therapy comprising a combined effective amount of eflornithine and sulindac, wherein the patient has an intact lower gastrointestinal tract or an at least partially intact lower gastrointestinal tract.

In some embodiments, the methods delay or even prevent FAP disease progression in the patient. For example, the methods may delay or even prevent the need for colon surgery or lower gastrointestinal tract surgery. As another example, the methods may delay or even prevent the formation of colorectal cancer in the patient.

In some embodiments, the methods delays or even prevents the need for excisional intervention. For example, the methods may prevent or delay the development of adenomas. In certain embodiments, the adenomas are high risk adenomas.

In some embodiments, the methods delay or even prevents polyposis progression. For example, the method delays the need for endoscopic excision or surgical resection for treatment of polyposis.

In some embodiments, the patient's genotype at position +263 (rs2302616) of at least one allele of the ODC1 gene has been determined. In certain embodiments, the patient's genotype has been determined to have a T at position +263 (rs2302616) of at least one allele of the ODC1 gene. For example, only patients having a T at position +263 (rs2302616) of at least one allele of the ODC1 gene are treated. In certain embodiments, the patient's genotype has been determined to have a T at position +263 (rs2302616) of both alleles of the ODC1 gene. In certain embodiments, the patient's genotype has been determined to have a T at position +263 (rs2302616) of one allele of the ODC1 gene and a G at position +263 (rs2302616) of one allele of the ODC1 gene. For example, only patients having a TT or TG genotype at position +263 (rs2302616) of the ODC1 gene are treated.

In some embodiments, the patient's genotype at position +316 (rs2302615) of at least one allele of the ODC1 gene has been determined. In certain embodiments, the patient's genotype has been determined to have a G at position +316 (rs2302615) of at least one allele of the ODC1 gene. For example, only patients having a G at position +316 (rs2302615) of at least one allele of the ODC1 gene are treated. In certain embodiments, the patient's genotype has been determined to have a G at position +316 (rs2302615) of both alleles of the ODC1 gene. In certain embodiments, the patient's genotype has been determined to have a G at position +316 (rs2302615) of one allele of the ODC1 gene and an A at position +316 (rs2302615) of one allele of the ODC1 gene. For example, only patients having a GG or GA genotype at position +316 (rs2302615) of the ODC1 gene are treated. As a further example, only patients having a TT or TG genotype at position +263 (rs2302616) of the ODC1 gene and a GG or GA genotype at position +316 (rs2302615) of the ODC1 gene are treated. In certain embodiments, the methods prevent ototoxicity or reduces the risk thereof within the patient.

In some embodiments, the eflornithine is eflornithine hydrochloride. In certain embodiments, the eflornithine hydrochloride is eflornithine hydrochloride monohydrate. In certain embodiments, the eflornithine hydrochloride monohydrate is a racemic mixture of its two enantiomers. In certain embodiments, the eflornithine hydrochloride monohydrate is a substantially optically pure preparation.

In some embodiments, the eflornithine is administered systemically. In certain embodiments, the eflornithine is administered orally, intraarterially or intravenously. In certain embodiments, the eflornithine is administered orally. In certain embodiments, the effective amount of eflornithine is 500-1500 mg/m$^2$/day. In certain embodiments, the eflornithine is formulated for oral administration. In certain embodiments, the eflornithine is formulated as a hard or soft capsule or a tablet. In some embodiments, the eflornithine is administered every 12 hours. In some embodiments, the eflornithine is administered every 24 hours. In some embodiments, the eflornithine is administered at least a second time.

In some embodiments, the sulindac is a metabolite of sulindac. In some embodiments, the sulindac is administered systemically. In certain embodiments, the sulindac is administered orally, intraarterially or intravenously. In certain embodiments, the sulindac is administered orally. In certain embodiments, the effective amount of sulindac is from about 10 to about 1500 mg/day. In certain embodiments, the effective amount of sulindac is from about 10 to about 400 mg/day. In certain embodiments, the effective amount of sulindac is 150 to 300 mg/day. In certain embodiments, the sulindac is formulated for oral administration. In certain embodiments, the sulindac is formulated as a hard or soft capsule or a tablet. In some embodiments, the sulindac is administered every 12 hours. In some embodiments, the sulindac is administered every 24 hours.

In some embodiments, the eflornithine and sulindac are administered simultaneously. In certain embodiments, the eflornithine and sulindac are administered in a single formulation, also referred to as a fixed dose combination. In certain embodiments, the single formulation is a single 700 mg tablet comprising 375 mg of eflornithine HCl monohydrate and 75 mg of sulindac. In certain embodiments, more than one tablet is administered at a time.

In some aspects of any of the above embodiments, the combined effective amount of eflornithine and sulindac is a fixed dose combination. In some aspects, the fixed dose combination comprises about 375 mg of eflornithine hydrochloride monohydrate. In some aspects, the fixed dose combination comprises about 288.6 mg of eflornithine in its anhydrous, free base form. In some aspects, the fixed dose combination comprises about 75 mg of sulindac. In some aspects, the eflornithine hydrochloride monohydrate is a racemic mixture of its two enantiomers. In some aspects, the amount of eflornithine hydrochloride monohydrate racemate is about 375 mg. In some aspects, the fixed dose combination further comprises an excipient, such as, for example, starch, colloidal silicon dioxide, or silicified microcrystalline cellulose. In some aspects, the excipient is colloidal silicon dioxide. In some aspects, the fixed dose combination further comprises a second excipient, such as, for example, silicified microcrystalline cellulose. In some aspects, the fixed dose combination further comprises a lubricant, such as, for example, magnesium stearate, calcium stearate, sodium stearate, glyceryl monostearate, aluminum stearate, polyethylene glycol, boric acid, or sodium benzoate. In some aspects, the lubricant is magnesium stearate. In some aspects, the amount of magnesium stearate is from about 1 to about 1.5 weight percent. In some aspects, the amount of magnesium stearate is about 1.5 weight percent. In some aspects, the fixed dose combination is in the form of a tablet. In some aspects, the weight of the tablet is from about 675 mg to about 725 mg. In some aspects, the weight of the tablet is about 700 mg. In some aspects, the tablet further comprises a coating, which comprises, for example, hydroxypropyl methylcellulose, titanium dioxide, polyethylene glycol, and iron oxide yellow. In some aspects, the coating masks the taste of eflornithine. In some aspects, the amount of coating is from about 2 to about 4 weight percent. In some aspects, the weight of the tablet is from about 700 mg to about 725 mg. In some aspects, the weight of the tablet is about 721 mg. In some aspects, the patient is administered two units of the fixed dose combination per day.

In some embodiments, the eflornithine and sulindac are administered consecutively. In certain embodiments, the eflornithine is administered prior to the sulindac. In certain embodiments, the eflornithine is administered after the sulindac.

In some embodiments, the patient is human.

In one aspect, provided are compositions comprising a combined pharmaceutically effective amount of eflornithine and sulindac for use in treating a patient having familial adenomatous polyposis (FAP), wherein the patient has an intact lower gastrointestinal tract or an at least partially intact lower gastrointestinal tract.

In one aspect, provided are combined pharmaceutically effective amounts of eflornithine and sulindac for use in the treatment of familial adenomatous polyposis (FAP) in patients having an intact lower gastrointestinal tract or an at least partially intact lower gastrointestinal tract.

In one aspect, provided are compositions comprising a combined pharmaceutically effective amount of eflornithine and sulindac for use in delaying or preventing a familial adenomatous polyposis (FAP) event and/or FAP progression in a patient with FAP, wherein the patient has an intact lower gastrointestinal tract or an at least partially intact lower gastrointestinal tract.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
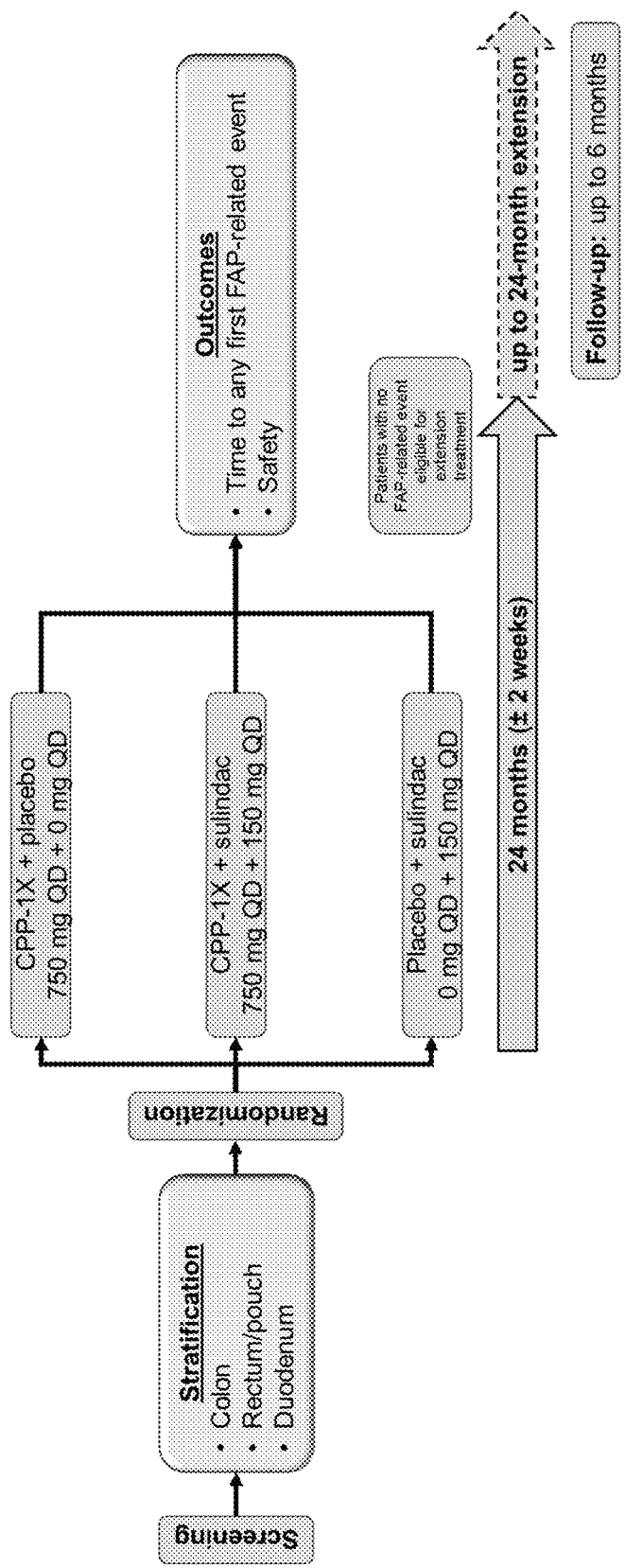
FIG. 1. FAP study design. FAP: familial adenomatous polyposis. QD: once daily.

Familial adenomatous polyposis (FAP) is an orphan disease with multiple major unmet medical needs. The current standard of practice involves prophylactic colectomy or proctocolectomy, followed by proctoscopic intervention with surgical polypectomies and/or laser/cautery ablation every 6-12 months for the rest of their lives. Many patients have extensive polyposis at a young age and require surgery prior to entering college. Following prophylactic colon surgery, follow-up intervention by proctoscopy and upper GI endoscopy occurs every 6-12 months and subsequent surgical interventions are generally performed at experienced centers of excellence, requiring frequent, inconvenient and expensive travel. The serial interventions are unpleasant, require dietary restriction and enemas. During surgical procedures, some patients require general anesthesia and all patients require sedation. Surgical procedures for large or multiple adenomas may involve snare cautery polypectomy or trans-anal excision and carry risk of bowel perforation and or subsequent bleeding. The greater the frequency and extent of the surgical procedures, the greater the morbidity and associated costs. Such interventions frequently result in reduced compliance with medical and surgical recommendations, with subsequent increased likelihood of the development of an interval cancer. In addition, repeated cautery ablations lead to scarring and impaired bowel function over the years.

Methods to defer or obviate the need for additional surgical interventions in patients with familial adenomatous polyposis are needed. Increasing the time to clinically meaningful FAP-related events (FAP-related surgery, duodenal polyposis, cancer and death) is a key factor in regard to decreasing the morbidity and mortality of this genetic disease. FAP related surgical or clinical events in the colon, rectum, or pouch include surgery related to large or high-risk adenomas or cancer.

Pharmacologic control in FAP patients has major implications for clinical benefit to reduce the morbidity of the disease and thereby improve the current standard of care. The use of low dose sulindac and eflornithine prolongs the time to occurrence of, or obviates the need for, clinically important FAP-related disease events, including surgical procedures. As such, the present methods can be used to defer the initial prophylactic colectomy to a more "convenient time" such as after graduation from school or after childbirth. The present methods can also be used to reduce the risk of progressive rectal/pouch polyposis that requires surgical intervention. The present methods may be beneficial in preventing or delaying FAP events or progression in the duodenum.

I. Familial Adenomatous Polyposis

Excess polyamine formation has long been implicated in epithelial carcinogenesis, particularly colorectal carcinogenesis. Polyamines are small ubiquitous molecules involved in various processes, including, for example, transcription, RNA stabilization, and ion channel gating (Wallace, 2000). Ornithine decarboxylase (ODC), the first enzyme in polyamine synthesis, is essential for normal development and tissue repair in mammals but is down-regulated in most adult tissues (Gerner and Meyskens, 2004). Multiple abnormalities in the control of polyamine metabolism and transport result in increased polyamine levels that can promote tumorigenesis in several tissues (Thomas and Thomas, 2003).

Familial adenomatous polyposis (FAP) is a syndrome associated with high risk of colon and other cancers. FAP is caused by mutations in the adenomatous polyposis coli (APC) tumor suppressor gene, and APC signaling has been shown to regulate ODC expression in both human cells (Fultz and Gerner, 2002) and in a mouse model of FAP (Erdman et al., 1999). Polyamine metabolism is up-regulated in intestinal epithelial tissues of humans with (Giardiello et al., 1997) FAP.

Wild type APC expression leads to decreased expression of ODC, while mutant APC leads to increased expression of ODC. The mechanism of APC-dependent regulation of ODC involves E-box transcription factors, including the transcriptional activator c-MYC and the transcriptional repressor MAD1 (Fultz and Gerner, 2002; Martinez et al., 2003). c-MYC was shown by others to regulate ODC transcription (Bellofernandez et al., 1993). Several genes involved in polyamine metabolism are essential genes for optimal growth in most organisms, and are down-regulated in non-proliferating and/or adult cells and tissues (Gerner and Meyskens, 2004). The polyamines influence specific cellular phenotypes, in part, by affecting patterns of gene expression, as reviewed elsewhere (Childs et al., 2003).

Familial Adenomatous Polyposis (FAP), an inherited polyposis syndrome, is the result of germ-line mutation of the adenomatous polyposis coli (APC) tumor suppressor gene (Su et al., 1992). This autosomal-dominant condition with variable expression is associated with the development of hundreds of colonic adenomas, which uniformly progress to adenocarcinoma by forty years of age, two decades earlier than the mean age diagnosis for sporadic colon cancer (Bussey, 1990). In prior studies of pre-symptomatic individuals with FAP, increased levels of the polyamines spermidine and spermine, and their diamine precursor putrescine, have been detected in normal-appearing colorectal biopsies when compared to normal family member controls (Giardiello et al., 1997). The activity of ornithine decarboxylase (ODC), the first and rate-limiting enzyme in mammalian polyamine synthesis, also is elevated in apparently normal colonic mucosal biopsies from FAP patients (Giardiello et al., 1997; Luk and Baylin, 1984). These findings are of interest as the polyamines are necessary for optimal cell proliferation (Pegg, 1986). Further, suppression of ODC activity, using the enzyme-activated irreversible inhibitor DFMO, inhibits colon carcinogenesis in carcinogen-treated rodents (Kingsnorth et al., 1983; Tempero et al., 1989).

The Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death. A combination therapy of DFMO and sulindac was shown to be effective in reducing adenomas in these mice. See U.S. Pat. No. 6,258,845 and Gerner and Meyskens, 2004, which are incorporated herein by reference.

II. Eflornithine

The term "eflornithine" when used by itself and free of context refers to 2,5-diamino-2-(difluoromethyl)pentanoic acid in any of its forms, including non-salt and salt forms (e.g., eflornithine HCl), anhydrous and hydrate forms of non-salt and salt forms (e.g., eflornithine hydrochloride monohydrate), solvates of non-salt and salts forms, its enantiomers (R and S forms, which may also by identified as d and l forms), and mixtures of these enantiomers (e.g., racemic mixture). By "substantially optically pure preparation" is meant a preparation of a first enantiomer which contains about 5% wt. or less of the opposite enantiomer. Specific forms of eflornithine include eflornithine hydrochloride monohydrate (i.e., CAS ID: 96020-91-6; MW: 236.65), eflornithine hydrochloride (i.e., CAS ID: 68278-23-9; MW: 218.63), and anhydrous free base eflornithine (i.e., CAS ID: 70052-12-9; MW: 182.17). Where necessary, the specific form of eflornithine has been further specified. In some embodiments, the eflornithine of the present disclosure is eflornithine hydrochloride monohydrate (i.e., CAS ID: 96020-91-6). The terms "eflornithine" and "DFMO" are used interchangeably herein. DFMO is an abbreviation for difluoromethylornithine. Other synonyms of eflornithine and DFMO include: α-difluoromethylornithine, 2-(difluoromethyl)-DL-ornithine, 2-(difluoromethyl)-dl-ornithine, 2-(Difluoromethyl) ornithine, DL-α-difluoromethylornithine, N-Difluoromethylornithine, αδ-diamino-α-(difluoromethyl)valeric acid, and 2,5-diamino-2-(difluoromethyl)pentanoic acid.

Eflornithine is an enzyme-activated, irreversible inhibitor of ornithine decarboxylase (ODC), the first and the rate limiting enzyme of the polyamine biosynthetic pathway (Meyskens & Gerner, 1999). As a result of this inhibition of polyamine synthesis, the compound is effective in preventing cancer formation in many organ systems, inhibiting cancer growth, and reducing tumor size. It also has synergistic action with other antineoplastic agents.

Eflornithine has been shown to decrease APC-dependent intestinal tumorigenesis in mice (Erdman et al., 1999). Oral eflornithine administered daily to humans inhibits ODC enzyme activity and polyamine contents in a number of epithelial tissues (Love et al., 1993; Gerner et al., 1994; Meyskens et al., 1994; Meyskens et al., 1998; Simoneau et al., 2001; Simoneau et al., 2008). Eflornithine in combination with the non-steroidal anti-inflammatory drug (NSAID) sulindac, has been reported to markedly lower the adenoma occurrence rate among individuals with colonic adenomas when compared to placebos in a randomized clinical trial (Meyskens et al., 2008).

Eflornithine was originally synthesized by Centre de Recherche Merrell, Strasbourg. Current U.S. Food and Drug Administration (FDA) approvals include:

African sleeping sickness. High dose systemic IV dosage form—not marketed (Sanofi/WHO)

Hirsutitis (androgen-induced excess hair growth) topical dosage form

While no oral formulations of eflornithine have yet been approved by the FDA, topical and injectable forms have been approved. Vaniqa® is a cream, which contains 15% w/w eflornithine hydrochloride monohydrate, corresponding to 11.5% w/w anhydrous eflornithine (EU), respectively 13.9% w/w anhydrous eflornithine hydrochloride (U.S.), in a cream for topical administration. This topical product does not result in systemic exposure to eflornithine. Ornidyl® is an eflornithine HCl solution suitable for injection or infusion. It is supplied in the strength of 200 mg eflornithine hydrochloride monohydrate per ml (20 g/100 mL). DFMO combined with non-steroidal anti-inflammatory drugs, such as a tablet containing 375 mg Eflornithine HCL and 75 mg sulindac, are being developed under IND 103,678. Additional DFMO dosage forms are in development in the U.S. under IND 107,343, including a 250-mg tablet (Eflornithine HCl, monohydrate 250.00 mg) for use in adults and adolescents, and a DFMO powder (Eflornithine HCl, monohydrate) filled bottle for dilution, for use in pediatric populations.

Eflornithine and its use in the treatment of benign prostatic hypertrophy are described in U.S. Pat. Nos. 4,413,141, and 4,330,559. The '141 patent describes eflornithine as being a powerful inhibitor of ODC, both in vitro and in vivo. Administration of eflornithine is reported to cause a decrease in putrescine and spermidine concentrations in cells in which these polyamines are normally actively produced. Additionally, eflornithine has been shown to be capable of slowing neoplastic cell proliferation when tested in standard tumor models. The '559 patent describes the use of eflornithine and eflornithine derivatives for the treatment of benign prostatic hypertrophy. Benign prostatic hypertrophy, like many disease states characterized by rapid cell proliferation, is accompanied by abnormal elevation of polyamine concentrations.

Eflornithine can potentially be given continuously with significant anti-tumor effects. This drug is relatively non-toxic at low doses of 0.4 $g/m^2$/day to humans while producing inhibition of putrescine synthesis in tumors. Studies in a rat-tumor model demonstrate that eflornithine infusion can produce a 90% decrease in tumor putrescine levels without suppressing peripheral platelet counts.

Side effects observed with eflornithine include effects on hearing at high doses of 4 $g/m^2$/day that resolve when it is discontinued. These effects on hearing are not observed at lower doses of 0.4 $g/m^2$/day when administered for up to one year (Meyskens et al., 1994). In addition, a few cases of dizziness/vertigo are seen that resolve when the drug is stopped. Thrombocytopenia has been reported predominantly in studies using high "therapeutic" doses of eflornithine (>1.0 $g/m^2$/day) and primarily in cancer patients who had previously undergone chemotherapy or patients with compromised bone marrow. Although the toxicity associated with eflornithine therapy are not, in general, as severe as other types of chemotherapy, in limited clinical trials it has been found to promote a dose-related thrombocytopenia. Moreover, studies in rats have shown that continuous infusion of eflornithine for 12 days significantly reduces platelet counts compared with controls. Other investigations have made similar observations in which thrombocytopenia is the major toxicity of continuous i.v. eflornithine therapy. These findings suggest that eflornithine may significantly inhibit ODC activity of the bone marrow precursors of megakaryocytes. Eflornithine may inhibit proliferative repair processes, such as epithelial wound healing. A phase III clinical trial assessed the recurrence of adenomatous polyps after treatment for 36 months with eflornithine plus sulindac or matched placebos.

III. NSAIDs

NSAIDs are anti-inflammatory agents that are not steroids. In addition to anti-inflammatory effects, they are also reported to have analgesic, antipyretic, and platelet-inhibitory effects. They are used, for example, in the treatment of chronic arthritic conditions and certain soft tissue disorders associated with pain and inflammation. They have been reported to act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function. See AMA Drug Evaluations Annual, 1814-5, 1994.

The nonsteroidal anti-inflammatory drugs (NSAIDs), including aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model. NSAIDs also inhibit the development of tumors harboring an activated Ki-ras (Singh and Reddy, 1995). NSAIDs appear to inhibit carcinogenesis via the induction of apoptosis in tumor cells (Bedi et al., 1995; Lupulescu, 1996; Piazza et al., 1995; Piazza et al., 1997b). A number of studies suggest that the chemopreventive properties of the NSAIDs, including the induction of apoptosis, is a function of their ability to inhibit prostaglandin synthesis (reviewed in DuBois et al., 1996; Lupulescu, 1996; Vane and Botting, 1997). Studies, however, indicate that NSAIDs may act through both prostaglandin-dependent and -independent mechanisms (Alberts et al., 1995; Piazza et al., 1997a; Thompson et al., 1995; Hanif, 1996). Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a). Sulindac sulfone induces peroxisome proliferator-activated receptor-γ (PPAR), which binds to PPAR response elements for the spermidine/spermine acetyltransferase (SAT1) gene. Activation of this gene promotes the export of polyamines. This mechanism is complementary to the mechanism of eflornithine in reducing polyamine levels. Experimental findings in human cell and mouse models indicate that sulindac and other NSAIDS activate polyamine catabolism. Thus NSAIDs complement inhibitors of polyamine synthesis, like eflornithine to reduce tissue polyamines.

Several NSAIDs have been examined for their effects in human clinical trials. A phase IIa trial (one month) of ibuprofen was completed and even at the dose of 300 mg/day, a significant decrease in prostoglandin E2 (PGE2) levels in flat mucosa was seen. A dose of 300 mg of ibuprofen is very low (therapeutic doses range from 1200-3000 mg/day or more), and toxicity is unlikely to be seen, even over the long-term. However, in animal chemoprevention models, ibuprofen is less effective than other NSAIDs.

The methods provided herein may comprise administering pharmaceutically acceptable amounts of an NSAID, including, for example, any of the NSAIDs discussed herein.

A. Aspirin

Aspirin, also known as acetylsalicylic acid, is a salicylate drug, often used as an analgesic to relieve minor aches and pains, as an antipyretic to reduce fever, and as an anti-inflammatory medication. Aspirin was first isolated by Felix Hoffmann, a chemist with the German company Bayer in 1897. Salicylic acid, the main metabolite of aspirin, is an integral part of human and animal metabolism. While in humans much of it is attributable to diet, a substantial part is synthesized endogenously. Today, aspirin is one of the most widely used medications in the world, with an estimated 40,000 tons of it being consumed each year. In countries where Aspirin is a registered trademark owned by Bayer, the generic term is acetylsalicylic acid (ASA).

Aspirin also has an antiplatelet effect by inhibiting the production of thromboxane, which under normal circumstances binds platelet molecules together to create a patch over damaged walls of blood vessels. Because the platelet patch can become too large and also block blood flow, locally and downstream, aspirin is also used long-term, at low doses, to help prevent heart attacks, strokes, and blood clot formation in people at high risk of developing blood clots. It has also been established that low doses of aspirin may be given immediately after a heart attack to reduce the risk of another heart attack or of the death of cardiac tissue. Aspirin may be effective at preventing certain types of cancer, particularly colorectal cancer.

The main undesirable side effects of aspirin taken by mouth are gastrointestinal ulcers, stomach bleeding, and tinnitus, especially in higher doses. In children and adolescents, aspirin is no longer indicated to control flu-like symptoms or the symptoms of chickenpox or other viral illnesses, because of the risk of Reye's syndrome.

Aspirin is part of a group of medications called nonsteroidal anti-inflammatory drugs (NSAIDs), but differs from most other NSAIDS in the mechanism of action. Though aspirin, and others in its group called the salicylates, have similar effects (antipyretic, anti-inflammatory, analgesic) to the other NSAIDs and inhibit the same enzyme cyclooxygenase, aspirin (but not the other salicylates) does so in an irreversible manner and, unlike others, affects more the COX-1 variant than the COX-2 variant of the enzyme.

B. Sulindac and Its Major Metabolites, Sulindac Sulfone and Sulindac Sulfide

Sulindac is a non-steroidal anti-inflammatory drug (NSAID) that exhibits anti-inflammatory, analgesic and anti-pyretic activities in animal models. In addition to these properties, it has been shown to be an antitumor agent. Based on both genetic and pharmacological studies, it is suggested that the antitumor effects are mediated, at least in part, through inhibition of cyclooxygenases (COX), the rate-limiting enzyme in prostaglandin biosynthesis. There are at least two distinct forms, COX-1 and COX-2. Physiologically sulindac is metabolized into sulfide- or sulfone containing derivatives. Both derivatives inhibit growth and induce apoptosis in a variety of human tumor-derived cell lines. The sulfide derivative inhibits colon carcinogenesis by inhibiting COX-1 and COX-2 enzyme activities. However, sulindac sulfone also inhibits chemical carcinogenesis in rodents but by a mechanism that cannot be explained solely by the inhibition of prostaglandin synthesis (Hwang et al., 2002). Sulindac sulfone induces peroxisome proliferator-activated receptor-γ (PPAR), which binds to PPAR response elements (PPREs) for the spermidine/spermine acetyltransferase (SAT1) gene (Babbar et al., 2003). Activation of this gene promotes the export of polyamines. This mechanism is complementary to the mechanism of eflornithine in reducing polyamine levels (Gerner & Meyskens, 2009). Experimental findings in human cell and mouse models indicate that sulindac and other NSAIDS activate polyamine catabolism (Gerner & Meyskens, 2009). Thus, NSAIDs complement inhibitors of polyamine synthesis, like eflornithine to reduce tissue polyamines.

Sulindac is a nonsteroidal, anti-inflammatory indene derivative with the following chemical designation; (Z)-5-fluoro-2-methyl-1-((4-(methylsulfinyl)phenyl)methylene)-1H-indene-3-acetic acid (Physician's Desk Reference, 1999). Without being bound by theory, the sulfinyl moiety is converted in vivo by reversible reduction to a sulfide metabolite and by irreversible oxidation to a sulfone metabolite (exisulind). See U.S. Pat. No. 6,258,845, which is incorporated herein by reference in its entirety. Sulindac, which also inhibits Ki-ras activation, is metabolized to two different molecules which differ in their ability to inhibit COX, yet both are able to exert chemopreventive effects via the induction of apoptosis. Sulindac sulfone lacks COX-inhibitory activity, and most likely facilitates the induction of apoptosis in a manner independent of prostaglandin synthesis. Available evidence indicates that the sulfide derivative is at least one of the biologically active compounds. Based on this, sulindac may be considered a prodrug.

Sulindac (Clinoril®) is available, for example, as 150 mg and 200 mg tablets. The most common dosage for adults is 150 to 200 mg twice a day, with a maximal daily dose of 400 mg. After oral administration, about 90% of the drug is absorbed. Peak plasma levels are achieved in about 2 hours in fasting patients and 3 to 4 hours when administered with food. The mean half-life of sulindac is 7.8 hours: the mean half-life of the sulfide metabolite is 16.4 hours. U.S. Pat. Nos. 3,647,858 and 3,654,349 cover preparations of sulindac, both are incorporate by reference herein in their entireties.

Sulindac is indicated for the acute and long-term relief of signs and symptoms of osteoarthritis, rheumatoid arthritis, ankylosing spondylitis, acute gout, and acute painful shoulder. The analgesic and antiinflammatory effects exerted by sulindac (400 mg per day) are comparable to those achieved by aspirin (4 g per day), ibuprofen (1200 mg per day), indomethacin (125 mg per day), and phenylbutazone (400 to 600 mg per day). Side effects of sulindac include mild gastrointestinal effects in nearly 20% of patients, with abdominal pain and nausea being the most frequent complaints. CNS side effects are seen in up to 10% of patients, with drowsiness, headache, and nervousness being those most frequently reported. Skin rash and pruritus occur in 5% of patients. Chronic treatment with sulindac can lead to serious gastrointestinal toxicity such as bleeding, ulceration, and perforation.

The potential use of sulindac for chemoprevention of cancers, and in particular colorectal polyps, has been studied. Two recent U.S. Pat. Nos. 5,814,625 and 5,843,929, detail potential chemopreventive uses of sulindac in humans. Both patents are incorporated herein in their entireties. Doses of sulindac claimed in U.S. Pat. No. 5,814,625 range from 10 mg to 1500 mg per day, with preferred doses of 50 mg to 500 mg per day. However, at the higher doses, the biggest problem with the use of sulindac as a single agent in chemoprevention is its well-known toxicities and moderately high risk of intolerance. The elderly appear to be especially vulnerable, as the incidence of side effects is higher in those over the age of 60. It is noted that this age group is most likely to develop colorectal cancer, and therefore, most likely to benefit from chemoprevention. Sulindac has been shown to produce regression of adenomas in Familial Adenomatous Polyposis (FAP) patients (Muscat et al., 1994), although at least one study in sporadic adenomas has shown no such effect (Ladenheim et al., 1995). Sulindac and its sulfone metabolite exisulind have been tested.

A combination therapy of DFMO and sulindac was shown to be effective in reducing adenomas in these mice. See U.S. Pat. No. 6,258,845, which is incorporated herein by reference in its entirety.

C. Piroxicam

Piroxicam is a non-steroidal anti-inflammatory agent that is well established in the treatment of rheumatoid arthritis and osteoarthritis with the following chemical designation: 4 hydroxy-2-methyl-N-2-pyridyl-2H-1,2-benzothiazine-3-carboxamide 1,1-dioxide. Its usefulness also has been demonstrated in the treatment of musculoskeletal disorders, dysmenorrhea, and postoperative pain. Its long half-life enables it to be administered once daily. The drug has been shown to be effective if administered rectally. Gastrointestinal complaints are the most frequently reported side effects.

Piroxicam has been shown to be effective chemoprevention agent in animal models (Pollard and Luckert, 1989; Reddy et al., 1987), although it demonstrated side effects in a recent IIb trial. A large meta-analysis of the side effects of the NSAIDs also indicates that piroxicam has more side effects than other NSAIDs (Lanza et al., 1995).

The combination of DFMO and piroxicam has been shown to have a synergistic chemopreventive effect in the AOM-treated rat model of colon carcinogenesis (Reddy et al., 1990), although DFMO exerted a greater suppressive effect than piroxicam on Ki-ras mutation and tumorigenesis when each agent was administered separately (Reddy et al., 1990). In one study, administration of DFMO or piroxicam to AOM-treated rats reduced the number of tumors harboring Ki-ras mutations from 90% to 36% and 25%, respectively (Singh et al., 1994). Both agents also reduced the amount of biochemically active p21 ras in existing tumors.

D. Celecoxib

Celecoxib is a non-steroidal anti-inflammatory agent that is well established in the treatment of osteoarthritis, rheumatoid arthritis, acute pain, ankylosing spondylitis, and to reduce the number of colon and rectal polyps in patients with FAP with the following chemical designation: 4-[5-(4-Methylphenyl)-3-(trifluoromethyl)pyrazol-1-yl]benzenesulfonamide. Celecoxib is marketed under the brand names Celebrex, Celebra, and Onsenal by Pfizer. Celecoxib is a selective COX-2 inhibitor. Side effects of celecoxib include a 30% increase in rates of heart and blood vessel disease. Additionally, the risk of gastrointestinal side effects are greater than 80%.

E. Combinations of NSAIDs

Combinations of various NSAIDs are also used for various purposes. By using lower doses of two or more NSAIDs, it is possible to reduce the side effects or toxicities associated with higher doses of individual NSAIDs. For example, in some embodiments, sulindac may be used together with celecoxib. In some embodiments, the one or both of the NSAIDS are selective COX-2 inhibitors. Examples of NSAIDS that back be used either alone or in combination include, but are not limited to, the following: ibuprofen, naproxen, fenoprofen, ketoprofen, flurbiprofen, oxaprozin, indomethacin, sulindac, etodolac, diclofenac, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, or etoricoxib.

F. Combinations of NSAIDs and Eflornithine

Preclinical studies, investigating the anti-carcinogenic effects of eflornithine combined with a number of NSAIDS, have been reported. Notably, eflornithine combined with sulindac is a potent inhibitor of chemical carcinogen-induced colon carcinogenesis in mice (Legendre-McGee et al., 2015). Eflornithine combined with either sulindac or celecoxib effectively reduced intestinal carcinogenesis in the Apc$^{Min/+}$ mouse model of the human syndrome familial adenomatous polyposis (FAP) (Ignatenko et al., 2008). Combination eflornithine and sulindac reduced metachronous colorectal adenomas by over 70%, compared to placebo, in a randomized clinical trial in patients with prior sporadic colorectal polyps (Meyskens et al., 2008). Combination eflornithine and celecoxib reduced the number of colonic adenomas by 13%, compared to a 1% reduction caused by celecoxib alone, in a randomized clinical trial in patients with FAP (Lynch et al., 2016). This reduction was not statistically significant in this clinical trial with small patient numbers. However, the combination therapy reduced measures of global tumor burden by over 80% from baseline, compared to 30% by celecoxib alone, and this difference was statistically significant.

IV. Eflornithine/Sulindac Combination Therapy

In some aspects, the methods provided herein may be used to treat familial adenomatous polyposis (FAP) and/or prevent or delay the need for colon surgery. In some aspects, the present methods comprise administering a fixed dose combination of a pharmaceutically effective amount of eflornithine and a pharmaceutically effective amount of a nonsteroidal anti-inflammatory drug (NSAID) or a metabolite thereof. In some embodiments, the fixed dose combination is a pharmaceutically effective amount of eflornithine and a pharmaceutically effective amount of sulindac. Examples of such fixed dose combination are provided in International PCT Publication Number WO 2017/075576, which is incorporated by reference herein in its entirety. In some aspects, the present methods comprise separately administering a pharmaceutically effective amount of eflornithine and a pharmaceutically effective amount of a nonsteroidal anti-inflammatory drug (NSAID) or a metabolite thereof.

In some embodiments, the agent(s) may be administered on a routine schedule. As used herein, a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agents can be taken every morning and/or every evening, regardless of when the subject has eaten or will eat.

V. Diagnosis and Treatment of Patients

In some embodiments, the treatment methods may be supplemented with diagnostic methods to improve the efficacy and/or minimize the toxicity of the anti-cancer therapies comprising administration of the compositions provided herein. Such methods are described, for example, in U.S. Pat. Nos. 8,329,636 and 9,121,852, U.S. Patent Publications US2013/0217743 and US2015/0301060, and PCT Patent Publications WO2014/070767 and WO2015/195120, which are all incorporated herein by reference.

In some embodiments, compositions and formulations of the present disclosure may be administered to a subject with a genotype at position +316 (rs2302615) of at least one allele of the ODC1 gene promoter is G. In some embodiments, the genotype at position +316 of both alleles of the patient's ODC1 gene promoters may be GG. In some embodiments, the genotype at position +316 (rs2302615) of both alleles of the patient's ODC1 gene promoters may be GA. A statistically significant interaction was detected for ODC1 genotype and treatment in a full model for adenoma recurrence, such that the pattern of adenoma recurrence among placebo patients was: GG 50%, GA 35%, AA 29% versus eflornithine/sulindac patients: GG 11%, GA 14%, AA 57%. Here, adenoma recurrence refers to a metachronous adenoma rather than recurrence of the original adenoma. The adenoma-inhibitory effect of eflornithine and sulindac was greater among those with the major G homozygous ODC1 genotype, in contrast to prior reports showing decreased risk of recurrent adenoma among CRA patients receiving aspirin carrying at least one A allele (Martinez et al., 2003; Barry et al., 2006; Hubner et al., 2008). These results demonstrate that ODC1 A allele carriers at position +316 (rs2302615) differ in response to prolonged exposure with eflornithine and sulindac compared to GG genotype patients, with A allele carriers experiencing less benefit in terms of adenoma recurrence, and potential for elevated risk of developing ototoxicity, especially among the AA homozygotes.

In some embodiments, the invention provides methods for the preventative or curative treatment of colorectal carcinoma in a patient comprising: (a) obtaining results from a test that determines the patient's genotype at position +316 (rs2302615) of at least one ODC1 promoter gene allele; and (b) if the results indicate that the patient's genotype at position +316 (rs2302615) of at least one allele of the ODC1 promoter gene is G, then administering to the patient a composition provided herein. In some embodiments, the invention provides methods for the treatment of colorectal carcinoma risk factors in a patient comprising: (a) obtaining results from a test that determines the patient's genotype at position +316 (rs2302615) of at least one ODC1 promoter gene allele; and (b) if the results indicate that the patient's genotype at position +316 (rs2302615) of at least one allele of the ODC1 promoter gene is G, then administering to the patient a composition provided herein, wherein the methods prevent the formation of new aberrant crypt foci, new adenomatous polyps or new adenomas with dysplasia in the patient. See U.S. Pat. No. 8,329,636, which is incorporated herein by reference.

In some embodiments, the invention provides methods for the preventative or curative treatment of familial adenomatous polyposis (FAP) in a patient comprising: (a) obtaining results from a test that determines the patient's genotype at position +316 (rs2302615) of at least one ODC1 promoter gene allele; and (b) if the results indicate that the patient's genotype at position +316 (rs2302615) of at least one allele of the ODC1 promoter gene is G, then administering to the patient a composition provided herein. In some embodiments, the invention provides methods for the treatment of familial adenomatous polyposis risk factors in a patient comprising: (a) obtaining results from a test that determines the patient's genotype at position +316 (rs2302615) of at least one ODC1 promoter gene allele; and (b) if the results indicate that the patient's genotype at position +316 (rs2302615) of at least one allele of the ODC1 promoter gene is G, then administering to the patient a composition provided herein, wherein the methods prevent the formation of new aberrant crypt foci, new adenomatous polyps or new adenomas with dysplasia in the patient. See U.S. Pat. No. 9,121,852, which is incorporated herein by reference.

In some embodiments, the invention provides methods for treating patients with FAP comprising administering to the patients a composition provided herein, wherein the patients have been determined to have a dietary polyamine intake, and/or tissue polyamine level, and/or tissue polyamine flux that is not high. In some of these embodiments, the dietary polyamine intake that is not high is 300 µM polyamine per day or lower. In some of these embodiments, the carcinoma is colorectal cancer. See U.S. Patent Publication US2013/0217743, which is incorporated herein by reference.

In some embodiments, the invention provides methods for the treatment of FAP in a patient comprising: (a) obtaining results from a test that determines an expression level of a let-7 non-coding RNA, a HMGA2 protein, and/or a LIN28 protein in a colon polyp cell from the patient; and (b) if the results indicate that the patient's cell exhibits a reduced let-7 non-coding RNA expression level as compared to a reference let-7 non-coding RNA expression level, an elevated HMGA2 protein expression level as compared a reference HMGA2 protein expression level, and/or an elevated LIN28 protein expression level as compared to a reference LIN28 protein expression level, then administering to the patient a composition provided herein. In some of these embodiments, the reference level is a level observed in a non-diseased subject or a level observed in a non-cancerous cell from the patient. In some of these embodiments, "obtaining" comprises providing a sample of a colon polyp from the patient and assessing an expression level of a let-7 non-coding RNA, an HMGA2 protein, or a LIN28 protein in a cell from the sample. In some of these embodiments, "assessing an expression level of a let-7 non-coding RNA" comprises quantitative PCR or Northern blotting. In some of these embodiments, "assessing an expression level of a HMGA2 protein or a LIN28 protein" comprises immunohistochemistry or ELISA. In some of these embodiments, the methods further comprise (c) obtaining results from a test that determines the expression of a let-7 non-coding RNA in a second cell from said patient at a second time point following the administration of at least one dose of the ODC inhibitor. In some of these embodiments, the methods further comprise increasing the amount of the ODC inhibitor administered to the patient if no or a small increase in let-7 non-coding RNA is observed. In some of these embodiments, the methods further comprise obtaining results from a test that determines the expression of a HMGA2 protein or a LIN28 protein in a second cell from said patient at a second time point following the administration of at least one dose of the ODC inhibitor. In some of these embodiments, the methods further comprise increasing the amount of the ODC inhibitor administered to the patient if no or a small decrease in HMGA2 protein or LIN28 protein is observed. In some of these embodiments, the methods further comprise (i) obtaining results from a test that determines the patient's genotype at position +316 of at least one allele of the ODC1 gene promoter; and (ii) if the results indicate that the patient's genotype at position +316 of at least one allele of the ODC1 gene promoter is G, then administering to the patient a composition provided herein. See U.S. Patent Publication US2015/0301060, which is incorporated herein by reference.

In some embodiments, there are provided methods for the treatment of FAP in a patient comprising: (a) obtaining results from a test that determines the patient's genotype at position +263 (rs2302616) of at least one ODC1 allele; and (b) if the results indicate that the patient's genotype at position +263 (rs2302616) of at least one allele of the ODC1 gene is T, then administering to the patient a composition provided herein. In some of these embodiments, the test may determine the nucleotide base at position +263 (rs2302616) of one allele of the ODC1 gene in the patient. In some embodiments, the test may determine the nucleotide bases at position +263 (rs2302616) of both alleles of the ODC1 gene in the patient. In some embodiments, the results may indicate that the patient's genotype at position +263 (rs2302616) of both alleles of the ODC1 gene is TT. In some embodiments, the results may indicate that the patient's genotype at position +263 (rs2302616) of both alleles of the ODC1 gene is TG. In some of these embodiments, the method may further comprise obtaining results from a test that determines the patient's genotype at position +316 (rs2302615) of at least one ODC1 allele and only administering to the patient of the composition provided herein if the results indicate that the patient's genotype at position +316 (rs2302615) of at least one allele of the ODC1 gene is G. In another aspect, there are provided methods for the treatment of colorectal carcinoma risk factors in a patient comprising: (a) obtaining results from a test that determines the patient's genotype at position +263 (rs2302616) of at least one ODC1 allele; and (b) if the results indicate that the patient's genotype at position +263 (rs2302616) of at least one allele of the ODC1 gene is T, then administering to the patient a composition provided herein, wherein the method prevents the formation of new aberrant crypt foci, new adenomatous polyps or new adenomas with dysplasia in the patient. In another aspect, there is provided methods for preventing the development of a carcinoma in a patient at risk therefor comprising: (a) obtaining results from a test that determines the patient's genotype at position +263 (rs2302616) of at least one ODC1 allele; and (b) if the results indicate that the patient's genotype at position +263 (rs2302616) of at least one allele of the ODC1 gene is T, then administering to the patient a composition provided herein. See PCT Patent Publication WO2015/195120, which is incorporated herein by reference.

In variations on any of the above embodiments, the methods may prevent the formation of new advanced colorectal neoplasms within the patient. In some embodiments, the method may prevent the formation of new right-sided advanced colorectal neoplasms. In some embodiments, the method may prevent the formation of new left-sided advanced colorectal neoplasms.

In variations on any of the above embodiments, the patient is human.

VI. Pharmaceutical Formulations and Routes of Administration

In one aspect, the present invention comprises administering compositions comprising a fixed dose combination of a pharmaceutically effective amount of eflornithine and a pharmaceutically effective amount of a nonsteroidal anti-inflammatory drug (NSAID) or a metabolite thereof. In some embodiments, the fixed dose combination is a pharmaceutically effective amount of eflornithine and a pharmaceutically effective amount of sulindac. In other aspects, the present invention comprises administering separation compositions comprising a fixed dose of a pharmaceutically effective amount of eflornithine and a fixed dose of a pharmaceutically effective amount of a nonsteroidal anti-inflammatory drug (NSAID) or a metabolite thereof.

In some embodiments, the eflornithine is eflornithine hydrochloride monohydrate. In some embodiments, the eflornithine is eflornithine hydrochloride monohydrate racemate. In some embodiments, the eflornithine hydrochloride monohydrate is a racemic mixture of its two enantiomers.

In some embodiments, the eflornithine is present in an amount of about 10 to about 1000 mg. In some embodiments, the eflornithine is present in an amount of about 250 to about 500 mg. In some embodiments, the eflornithine is present in an amount of about 300 to about 450 mg. In some embodiments, the eflornithine is present in an amount of about 350 to about 400 mg. In some embodiments, the eflornithine is present in an amount of about 35 to about 60 weight percent. In some embodiments, the eflornithine is present in an amount of about 40 to about 55 weight percent. In some embodiments, the eflornithine is present in an amount of about 50 to about 55 weight percent. In some embodiments, the eflornithine is present in an amount of about 52 to about 54 weight percent. In some embodiments, the amount of eflornithine hydrochloride monohydrate racemate is from 52 to 54 weight percent. In some embodiments, the eflornithine is present in an amount of about 375 mg. In some embodiments, the amount of eflornithine hydrochloride monohydrate racemate is 375 mg.

In some embodiments, the sulindac is present in an amount from about 10 to about 1500 mg. In some embodiments, the sulindac is present in an amount of about 50 to about 100 mg. In some embodiments, the sulindac is present in an amount of about 70 to about 80 mg. In some embodiments, the sulindac is present in an amount of about 75 mg. In some embodiments, the amount of sulindac is 75 mg. In some embodiments, the sulindac is present in an amount of about 5 to about 20 weight percent. In some embodiments, the sulindac is present in an amount of about 8 to about 15 weight percent. In some embodiments, the sulindac is present in an amount of about 10 to about 12 weight percent. In some embodiments, the amount of sulindac is from 10 to 11 weight percent.

In some embodiments, the eflornithine is present in an amount of about 375 mg and the sulindac is present in an amount of about 75 mg.

In some embodiments, the formulation further comprises an excipient. In some embodiments, the excipient is starch, colloidal silicon dioxide, or silicified microcrystalline cellulose. In some embodiments, the excipient is colloidal silicon dioxide. In some embodiments, the formulation further comprises a second excipient. In some embodiments, the second excipient is silicified microcrystalline cellulose.

In some embodiments, the formulation further comprises a lubricant. In some embodiments, the lubricant is magnesium stearate, calcium stearate, sodium stearate, glyceryl monostearate, aluminum stearate, polyethylene glycol, boric acid or sodium benzoate. In some embodiments, the lubricant is magnesium stearate. In some embodiments, magnesium stearate is present in an amount of about 0.25 to about 2 weight percent. In some embodiments, the amount of magnesium stearate is from about 0.75 to about 2 weight percent. In some embodiments, the amount of magnesium stearate is from about 1 to about 1.5 weight percent. In some embodiments, the amount of magnesium stearate is about 1.1 weight percent. In some embodiments, magnesium stearate is present in an amount of about 1.5 weight percent.

In some embodiments, the compositions are in the form of a capsule, tablet, mini tablets, granules, pellets, solution, gel, cream, foam or patch. In some embodiments, the composition is in the form of a tablet, for example, a monolayer tablet.

In some embodiments, the weight of the tablet is from about 650 mg to about 1,000 mg. In some embodiments, the weight of the tablet is from about 675 mg to about 725 mg. In some embodiments, the weight of the tablet is about 700 mg.

In some embodiments, the tablet further comprises a coating. In some embodiments, the coating is a modified release coating or an enteric coating. In some embodiments, the coating is a pH-responsive coating. In some embodiments, the coating comprises cellulose acetate phthalate (CAP), cellulose acetate trimelletate (CAT), poly (vinyl acetate) phthalate (PVAP), hydroxypropylmethylcellulose phthalate (HP), poly(methacrylate ethylacrylate) (1:1) copolymer (MA-EA), poly(methacrylate methylmethacrylate) (1:1) copolymer (MA MMA), poly(methacrylate methylmethacrylate) (1:2) copolymer, or hydroxypropylmethylcellulose acetate succinate (HPMCAS). In some embodiments, the coating masks the taste of eflornithine. In some embodiments, the coating comprises hydroxypropyl methylcellulose, titanium dioxide, polyethylene glycol, and iron oxide yellow.

In some embodiments, the amount of coating is from about 1 to about 5 weight percent. In some embodiments, the amount of coating is from about 2 to about 4 weight percent. In some embodiments, the amount of coating is about 3 weight percent. In some embodiments, the amount of coating is from about 5 mg to about 30 mg. In some embodiments, the amount of coating is from about 15 mg to about 25 mg. In some embodiments, the amount of coating is about 21 mg.

In some embodiments, the weight of the tablet comprising a coating is from about 675 mg to about 750 mg. In some embodiments, the weight of the tablet comprising a coating is from about 700 mg to about 725 mg. In some embodiments, the weight of the tablet comprising a coating is about 721 mg.

In one aspect, the present invention provides compositions comprising a fixed dose combination of a pharmaceutically effective amount of eflornithine and a pharmaceutically effective amount of sulindac. In some embodiments, the compositions are in the form of a capsule, tablet, mini tablets, granules, pellets, solution, gel, cream, foam or patch. In some embodiments, the compositions are solid and take the form of a tablet, for example, a monolayer tablet. In some embodiments, the tablet is film coated.

In some embodiments, the pharmaceutical compositions and formulations of the present invention are for enteral, such as oral, and also rectal or parenteral, with the compositions comprising the pharmacologically active compounds either alone or together with pharmaceutical auxiliary substances (excipients). Pharmaceutical preparations for enteral or parenteral administration are, for example, in unit dose forms, such as coated tablets, tablets, capsules or suppositories and also ampoules. These are prepared in a manner, which is known per se, for example using conventional mixing, granulation, coating, solubilizing or lyophilizing processes. Thus, pharmaceutical preparations for oral use can be obtained by combining the active compounds with solid excipients, if desired granulating a mixture which has been obtained, and, if required or necessary, processing the mixture or granulate into tablets or coated tablet cores after having added suitable auxiliary substances. In a preferred embodiment, a mixture of active ingredients and excipients are formulated into a tablet form. Appropriate coatings may be applied to increase palatability or delay absorption. For example, a coating may be applied to a tablet to mask the disagreeable taste of the active compound, such as eflornithine, or to sustain and/or to delay the release of the active molecules to a certain area in the gastrointestinal tract.

The therapeutic compounds can be orally administered, for example, with an inert diluent or an assimilable edible carrier. The therapeutic compounds and other ingredients may also be enclosed in a hard or soft shell gelatin capsule, compressed into tablets, or incorporated directly into the subject's diet. For oral therapeutic administration, the therapeutic compounds may be incorporated with excipients and used in the form of ingestible tablets, buccal tablets, troches, capsules, elixirs, suspensions, syrups, or wafers.

In certain embodiments, the tablets and/or capsules provided herein comprise the active ingredients and powdered carriers, such as lactose, starch, cellulose derivatives, magnesium stearate, and stearic acid. Similar diluents can be used to make compressed tablets. In other embodiments, tablets and capsules can be manufactured for immediate or modified release. In some embodiments, the tablet and/or capsule is manufactured as a sustained release product to provide for continuous release of medication over a period of hours. In some embodiments, the compressed tablet is sugar-coated and/or film-coated to mask unpleasant taste and/or protect the tablet from the atmosphere. In some embodiments, the tablet is enteric coated for selective disintegration in the gastrointestinal tract.

In some embodiments, the tablet or capsule is able to disintegrate or dissolve to liberate multiparticulates comprising particles of different populations of a first component and a second component, e.g. modified release coated multiparticles. In some of these embodiments, the tablet or capsule may disintegrate or dissolve in the mouth, stomach, small intestine, terminal ileum, or colon. In some of these embodiments, the tablet or capsule may release the multiparticulates with modified release properties.

In some embodiments, the present invention encompasses methods of administering a pharmaceutical oral fixed dose combination in the form of a multilayer tablet. A multilayer tablet has at least two layers (bilayer tablet) or can have three, four, five or more layers. In some embodiments, each of the layers contains not more than one of the active pharmaceutical ingredients (APIs). For example, in some embodiments, the tablet has two layers, with one of the APIs in each of the two layers. In some embodiments, in addition to these two layers, the tablet contains further layers containing only carrier and which may function, e.g., as separation layer(s) or outer coating layer(s). In some embodiments, if more than two layers are present, the components may be present in more than one layer as long as they are not present together in the same layer. In certain embodiments, a monolayer tablet is preferred but all information detailed below is equally applicable to multilayer tablets.

In some embodiments, the fixed dose combination may be formulated to provide a mean steady state plasma concentration level of total eflornithine and/or sulindac in the range of about 0.1 µM to about 1000 µM and preferably in the range of about 1 µM to 100 µM and more preferably in the range of about 1 µM to about 50 µM.

In some embodiments, the compositions further comprise a pharmaceutically acceptable excipient. In some of these embodiments, the pharmaceutically acceptable excipient may include a pharmaceutically acceptable diluent, a pharmaceutically acceptable disintegrant, a pharmaceutically acceptable binder, a pharmaceutically acceptable stabilizer, a pharmaceutically acceptable lubricant, a pharmaceutically acceptable pigment, or pharmaceutically acceptable glider. In a fixed dose combination formulation of the present invention, an active ingredient may be mixed at a weight ratio of 1:0.25 to 1:20 with a pharmaceutically acceptable excipient.

Diluents that can be used in pharmaceutical formulations of the present invention include, but are not limited to, microcrystalline cellulose ("MCC"), silicified MCC (e.g. PROSOLV™ HD 90), microfine cellulose, lactose, starch, pregelatinized starch, sugar, mannitol, sorbitol, dextrates, dextrin, maltodextrin, dextrose, calcium carbonate, calcium sulfate, dibasic calcium phosphate dihydrate, tribasic calcium phosphate, magnesium carbonate, magnesium oxide, and any mixtures thereof. Preferably, the diluent is silicified MCC. The diluent may be used in an amount of from about 5 to about 95 weight percent based on the total weight of the formulation, and preferably in an amount of from about 25 to about 40 percent weight, such as in an amount of from about 30 to about 35 percent weight. In certain aspects, the diluent can be a soluble diluent. When the diluent is used, its ratio to the active ingredient in each discrete layer is very important. The term "soluble diluents" refers to a diluent which is dissolved in water, like lactose, Ludipress (BASF, a mixture of lactose, crospovidone and povidone (93:3.5:3.5, w/w (%))), mannitol and sorbitol.

Disintegrants are used to promote swelling and disintegration of the tablet after exposure to fluids in the oral cavity and/or gastrointestinal tract. Examples of disintegrants useful in the fixed dose combination formulation of the present invention include crospovidone, sodium starch glycolate, croscarmellose sodium, low-substituted hydroxypropylcellulose, starch, alginic acid or sodium salt thereof, and a mixture thereof. Other disintegrants that can be used in pharmaceutical formulations of the present invention include, but are not limited to, methylcelluloses, microcrystalline celluloses, carboxymethyl cellulose calcium, carboxymethyl cellulose sodium (e.g. AC-DI-SOL™, PRIMELLOSE™), povidones, guar gum, magnesium aluminum silicate, colloidal silicon dioxide (e.g. AEROSIL™, CARBOSIL™), polacrilin potassium, starch, pregelatinized starch, sodium starch glycolate (e.g. EXPLOTAB™), sodium alginate, and any mixtures thereof. Preferably, the disintegrant is colloidal silicon dioxide. The disintegrant may be used in an amount of about 0.1 to about 30 weight percent based on the total weight of the formulation, and preferably in an amount of about 0.2 to about 5 weight percent.

Compositions of the present invention may comprise lubricants. Sticking can occur when granules attach themselves to the faces of tablet press punches. Lubricants are used to promote flowability of powders, and to reduce friction between the tablet punch faces and the tablet punches and between the tablet surface and the die wall. For example, lubricants include magnesium stearate, calcium stearate, zinc stearate, stearic acid, sodium stearyl fumarate, polyethylene glycol, sodium lauryl sulphate, magnesium lauryl sulphate, and sodium benzoate. Preferably, the lubricant is magnesium stearate. In the present invention, lubricants preferably comprise 0.25 weight percent to 2 weight percent of the solid dosage form, and preferably in an amount of about 1.5 weight percent. In an exemplary formulation, the lubricant is magnesium stearate present in an amount of about 1.5 weight percent to prevent sticking.

Binders can be used in the pharmaceutical compositions of the present invention to help hold tablets together after compression. Examples of binders useful for the present invention are acacia, guar gum, alginic acid, carbomers (e.g. Carbopol™ products), dextrin, maltodextrin, methylcelluloses, ethylcelluloses, hydroxyethyl celluloses, hydroxypropyl celluloses (e.g. KLUCEL™), hydroxypropyl methylcelluloses (e.g. METHOCEL™), carboxymethylcellulose sodiums, liquid glucose, magnesium aluminum silicate, polymethacrylates, polyvinylpyrrolidones (e.g., povidone K-90 D, KOLLIDON™), copovidone (PLASDONE™), gelatin, starches, and any mixtures thereof. Preferably, the binder is starch. In the present invention, binders preferably comprise about 1 to about 15 weight percent of the solid dosage form. In other embodiments, the solid dosage form does not comprise a binder.

In certain embodiments, the stabilizer usable in the fixed dose combination formulation of the present invention may be an anti-oxidant. The use of an antioxidant enhances stability of the active ingredients against the undesirable reaction with other pharmaceutically acceptable additives and against modification by heat or moisture with time. For example, the anti-oxidant is ascorbic acid and its esters, butylated hydroxytoluene (BHT), butylated hydroxyanisole (BHA), α-tocopherol, cystein, citric acid, propyl gallate, sodium bisulfate, sodium pyrosulfite, ethylene diamine tetracetic acid (EDTA), and any mixtures thereof.

VII. Methods of Treating

Effective combination therapy with eflornithine and sulindac may be achieved using two formulations: one that provides eflornithine and sulindac in a combined dosage form, or one that provides eflornithine and sulindac in separate dosage forms. In aspects involving two distinct compositions or formulations, each agent may be administered before, concurrently with, or following administration of the other agent. In some aspects, one would ensure that a significant period of time did not expire between the time of each delivery, such that each agent would still be able to exert an advantageously combined effect. In such instances, it is contemplated that one would typically administer each agent within about 12-24 hours of the others and, more preferably, within about 6-12 hours of each other.

In some embodiments, the agents may be administered on a routine schedule. As used herein, a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

In some embodiments, the agents may be administered in combination with at least a third agent. The at least third therapy may precede or follow treatment with eflornithine and sulindac by intervals ranging from minutes to months. In some aspects, one would ensure that a significant period of time did not expire between the time of each delivery, such that the combination of agents would still be able to exert an advantageously combined effect. In such instances, it is contemplated that one would typically administer the combination of eflornithine and sulindac and the at least third therapeutic agent within about 12-24 hours of each other and, more preferably, within about 6-12 hours of each other. In some aspects, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, such as where "A" represents the combination of eflornithine and sulindac and "B" represents the at least third agent, non-limiting examples of which are described below:

| A/B/A | B/A/B | B/B/A | A/A/B | A/B/B | B/A/A | A/B/B/B | B/A/B/B |
| B/B/B/A | B/B/A/B | A/A/B/B | A/B/A/B | | A/B/B/A | | B/B/A/A |
| B/A/B/A | B/A/A/B | A/A/A/B | B/A/A/A | | A/B/A/A | | A/A/B/A |

It is contemplated that agents that modulate the polyamine pathway may be used in conjunction with the treatments of the current invention. For example, additional non-steroidal anti-inflammatory drugs (NSAIDs), polyamine transporter inhibitors, eIF-5A antagonists, chemotherapeutic agents, radiotherapy, and immunomodulatory agents may be used.

A. NSAIDs

NSAIDs are anti-inflammatory agents that are not steroids. In addition to anti-inflammatory actions, they have analgesic, antipyretic, and platelet-inhibitory actions. They are used primarily in the treatment of chronic arthritic conditions and certain soft tissue disorders associated with pain and inflammation. They act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function. Examples of NSAIDS that may be used include, but are not limited to, aspirin, ibuprofen, naproxen, fenoprofen, ketoprofen, flurbiprofen, oxaprozin, indomethacin, etodolac, diclofenac, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib parecoxib, lumiracoxib, and etoricoxib.

B. Polyamine Transporter Inhibitors

Inhibitors of the polyamine transport include, but are not limited to, 4-bis(3-aminopropyl)-piperazine (BAP) and compounds disclosed in U.S. Patent Publn. No. 2011/0256161 (e.g., AMXT1501); U.S. Patent Publn. No. 2012/0172449; PCT Publn. No. WO 1999/054283; U.S. Pat. Nos. 6,083,496; and 5,456,908.

C. eIF-5A Antagonists

Hypusine (NE-(4-amino-2(R)-hydroxybutyl) lysine) is a unique amino acid that is formed on a synthesized protein by posttranslational modification. Hypusine is only known to occur in a single protein, eukaryotic translation initiation factor 5A (eIF-5A). The formation of hypusine occurs by two distinct steps involving modification of a single lysyl amino acid residue on the eIF-5A protein. This process is required for the biosynthesis of bioactive eIF-5A. Inhibitors of this process include, but are not limited to, N1-guanyl-1,7-diaminoheptane (GC7), and proteasome inhibitors (e.g., bortezomib, disulfiram, epigallocatechin-3-gallate, salinosporamide, carfilzomib, ONX 0912, CEP-18770, MLN9708, and epoxomicin).

D. Chemotherapeutic Agents

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaII); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarb azine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; retinoids, such as retinoic acid; carboplatin, procarbazine, plicomycin, gemcitabien, navelbine, farnesyl-protein tansferase inhibitors, PI3K inhibitors (e.g., perifosine, idelalisib, PX-866, IPI-145, BAY 80-6946, BEZ235, RP6530, TGR 1202, SF1126, INK1117, GDC-0941 BKM120, XL147 (also known as SAR245408), XL765 (also known as SAR245409), palomid 529, GSK1059615, ZSTK474, PWT33597, IC87114, TG100-115, CAL263, RP6503, PI-103, GNE-477, CUDC-907, AEZS-136), aurora kinase inhibitors (e.g., ZM447439, hesperadin, VX-680, and those disclosed in U.S. Pat. No. 8,815,872 and WO 2012/135641), transplatinum, and pharmaceutically acceptable salts, acids, or derivatives of any of the above.

E. Immunomodulatory Agents

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule (e.g., an anti-GD2 chimeric antigen receptor) that interacts, either directly or indirectly, with a tumor cell target. See, e.g., U.S. Patent Publn. No. 2014/0004132. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include GD2, CD20, carcinoembryonic antigen, tyrosinase (p9'7), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; U.S. Pat. Nos. 5,830,880 and 5,846,945); and monoclonal antibodies, e.g., anti-CD20, anti-ganglioside GM2, anti-GD2 [e.g., Ch14.18] (Yu et al., 2010; U.S. Patent Appln. Publn. Nos. 20130216528 and 20140170155; PCT Appln. Publn. WO 2014144763; U.S. Pat. Nos. 6,451,995, 8,507,657 and 8,278,065), and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer*, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) *Proc Natl Acad Sci USA* 95(17): 10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering (Park, Rosenberg et al. 2011). Isolation and transfer of tumor specific T cells has been shown to be successful in treating melanoma. Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors (Jena, Dotti et al. 2010).

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

F. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

G. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

H. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

VIII. Definitions

As used herein the specification, "a" or "an" may mean one or more. As used herein in the claim(s), when used in conjunction with the word "comprising," the words "a" or "an" may mean one or more than one.

Throughout this application, the term "about" is used to indicate that a value includes the inherent variation of error for the device, the method being employed to determine the value, or the variation that exists among the study subjects.

As used herein, the term "bioavailability" denotes the degree means to which a drug or other substance becomes available to the target tissue after administration. In the present context, the term "suitable bioavailability" is intended to mean that administration of a composition according to the invention will result in a bioavailability that is improved compared to the bioavailability obtained after administration of the active substance(s) in a plain tablet; or the bioavailability is at least the same or improved compared to the bioavailability obtained after administration of a commercially available product containing the same active substance(s) in the same amounts. In particular, it is desired to obtain quicker and larger and/or more complete uptake of the active compound, and thereby provide for a reduction of the administered dosages or for a reduction in the number of daily administrations.

The terms "compositions," "pharmaceutical compositions," "formulations," and "preparations" are used synonymously and interchangeably herein.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "derivative thereof" refers to any chemically modified polysaccharide, wherein at least one of the monomeric saccharide units is modified by substitution of atoms or molecular groups or bonds. In one embodiment, a derivative thereof is a salt thereof. Salts are, for example, salts with suitable mineral acids, such as hydrohalic acids, sulfuric acid or phosphoric acid, for example hydrochlorides, hydrobromides, sulfates, hydrogen sulfates or phosphates, salts with suitable carboxylic acids, such as optionally hydroxylated lower alkanoic acids, for example acetic acid, glycolic acid, propionic acid, lactic acid or pivalic acid, optionally hydroxylated and/or oxo-substituted lower alkanedicarboxylic acids, for example oxalic acid, succinic acid, fumaric acid, maleic acid, tartaric acid, citric acid, pyruvic acid, malic acid, ascorbic acid, and also with aromatic, heteroaromatic or araliphatic carboxylic acids, such as benzoic acid, nicotinic acid or mandelic acid, and salts with suitable aliphatic or aromatic sulfonic acids or N-substituted sulfamic acids, for example methanesulfonates, benzenesulfonates, p-toluenesulfonates or N-cyclohexylsulfamates (cyclamates).

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients in pharmaceutical contexts.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that the amount of the compound which, when administered to a subject or patient for treating or preventing a disease, is an amount sufficient to effect such treatment or prevention of the disease. As used herein, the term "IC50" refers to an inhibitory dose which is 50% of the maximum response obtained.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Prevention" or "preventing" includes: (1) inhibiting or delaying the onset or recurrence of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

The term "eflornithine" when used by itself refers to 2,5-diamino-2-(difluoromethyl)pentanoic acid is any of its forms, including non-salt and salt forms (e.g., eflornithine HCl), anhydrous and hydrate forms of non-salt and salt forms (e.g., eflornithine hydrochloride monohydrate), solvates of non-salt and salts forms, its enantiomers (R and S forms, which may also by identified as d and l forms), and mixtures of these enantiomers (e.g., racemic mixture, or mixtures enriched in one of the enantiomers relative to the other). Specific forms of eflornithine include eflornithine hydrochloride monohydrate (i.e., CAS ID: 96020-91-6; MW: 236.65), eflornithine hydrochloride (i.e., CAS ID: 68278-23-9; MW: 218.63), and free eflornithine (i.e., CAS ID: 70052-12-9; MW: 182.17). Where necessary, the form of eflornithine has been further specified. In some embodiments, the eflornithine of the present disclosure is eflornithine hydrochloride monohydrate (i.e., CAS ID: 96020-91-6). The terms "eflornithine" and "DFMO" are used interchangeably herein. Other synonyms of eflornithine and DFMO include: CPP-1X, α-difluoromethylornithine, 2-(Difluoromethyl)-DL-ornithine, 2-(Difluoromethyl)ornithine, DL-α-difluoromethylornithine, N-Difluoromethylornithine, ornidyl, αδ-Diamino-α-(difluoromethyl)valeric acid, and 2,5-diamino-2(difluro)pentanoic acid.

The term "fixed dose combination" or "FDC" refers to a combination of defined doses of two drugs or active ingredients presented in a single dosage unit (e.g., a tablet or a capsule) and administered as such; further as used herein, "free dose combination" refers to a combination of two drugs or active ingredients administered simultaneously but as two distinct dosage units.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, nanotubes, protein-DNA complexes, protein conjugates, erythrocytes, virosomes, and dendrimers.

The term "tablet" refers to a pharmacological composition in the form of a small, essentially solid pellet of any shape. Tablet shapes maybe cylindrical, spherical, rectangular, capsular or irregular. The term "tablet composition" refers to the substances included in a tablet. A "tablet composition constituent" or "tablet constituent" refers to a compound or substance which is included in a tablet composition. These can include, but are not limited to, the active and any excipients in addition to the low melting compound and the water-soluble excipient.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Unit abbreviations used herein include average result (ar), kilopond (kp), kilonewton (kN), percent weight per weight (% w/w), pounds per square inch (psi), RH (relative humidity), color difference delta E (dE), and revolutions per minute (rpm).

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Efficacy and Safety of Combined Eflornithine/Sulindac vs Eflornithine or Sulindac Alone in Patients with Familial Adenomatous Polyposis The eflornithine-sulindac combination was evaluated in patients with FAP. FAP patients are at elevated risk for intestinal and colorectal polyposis and other events related to the fact that they harbor germline mutations in the adenomatous polyposis coli (APC) tumor suppressor gene. These genotypic FAP patients express higher levels of the eflornithine target gene, ornithine decarboxylase (ODC) and polyamine contents in apparently normal rectal mucosa than do non-genotypic familial controls (Giardiello et al., 1997). These levels are higher than those reported for patients with sporadic risk of colorectal cancer (Hixson et al., 1993). For this trial, if a patient had not already been genotyped for FAP, genetic analysis was performed to confirm the presence of an APC mutation.

This randomized, double-blind, phase III trial compared the efficacy, safety and pharmacokinetics of the eflornithine (also referred to as CPP-1X) (750 mg/day)/sulindac (150 mg/day) combination versus eflornithine (CPP-1X) (750 mg/day) and sulindac (150 mg/day) as single agents with up to a 48-month maximum treatment period in patients with Familial Adenomatous Polyposis (FAP) (see FIG. 1). Subjects completing 24 months of treatment without an FAP-related event continued on treatment for up to 48 months until either the subject had an FAP-related even or the trial ended. Subjects were randomized to one of three treatment groups in equal proportions (i.e., 1:1:1 randomization): 1) CPP-1X plus sulindac 2) CPP-1X—placebo plus sulindac, 3) CPP-1X plus sulindac placebo. Patients underwent upper and lower gastrointestinal endoscopy every 6 months to assess disease status.

Adults aged ≥18 years with clinical FAP and pathogenic variants of APC and any of the following on baseline endoscopies were eligible for this study: (a) intact colon—moderate adenoma burden (100-1000 polyps) being considered for prophylactic surgery, (b) retained rectum or ileal pouch (≥3 years since ileorectal anastomosis (IRA)/IPAA surgery) with IRA or IPAA and International Society for Gastrointestinal Hereditary Tumours (InSiGHT) stage 1, 2 or 3 polyposis; excision of any polyp >1 cm at baseline, (Lynch et al., 2016) or (c) duodenum with Spigelman Stage III or IV polyposis or down-staged to Spigelman Stage I or II within the last 6 months (Saurin et al., 2004). Patients with significant cardiovascular risk factors (Zell et al., 2009) or clinically significant hearing loss requiring a hearing aid were not eligible. Patients were stratified by anatomic site with highest polyp burden and surgical status: (a) post colectomy with rectal or ileal pouch polyposis (longest projected time to first FRE); (b) with duodenal polyposis (intermediate projected time to first FRE); and (c) pre-colectomy (shortest projected time to first FRE) prior to randomization to minimize treatment imbalance.

A stratified randomization procedure was used with stratification based on FAP-related time-to-first-event prognosis (see FIG. 1). The event prognosis groups were represented by 1) best (i.e., longest projected time to first FAP-related event)—rectal/pouch polyposis (Post-colectomy (≥3 years S/P IRA or IPAA with >10 polyps; any polyps >5 mm excised at baseline)), 2) intermediate—duodenal polyposis (Spigelman Stage 3 or 4 or Spigelman Stage 3 or 4 down-staged to Spigelman 1 or 2 within the past 6 months), and 3) worst—pre-colectomy. If a subject has two or more of these disease sites, the most severe prognosis stratum was assigned for randomization (e.g. worst>intermediate>best). Since an individual may have more than one disease site involved, the trial assessed time to any defined FAP-related event in the subject as a whole. In order to minimize potential treatment arm imbalance a centralized randomization process was used to balance among treatment groups within prognostic strata.

Patients having major cardiovascular risk factors (e.g., history of stroke or myocardial infarction, moderate or severe heart failure) and/or hearing loss requiring a hearing aid were excluded from participation.

Lower GI Endoscopy: Patients were evaluated via colonoscopy, flexible or rigid procto-sigmoidoscopy during the screening phase. Biopsies, ablations, and snare excisions at baseline were performed per the clinician's standard of care. If considered eligible based on inclusion criteria, a grossly normal mucosa biopsy was obtained for baseline polyamine measurement. Still and video documentation of the colon (vide infra) or the residual rectum or entire pouch was also obtained for archiving. Polyp size was determined by visual comparison with biopsy forceps that can measure 5.0-5.5 mm in the fully open position. All randomized patients with an intact colon or rectum/pouch had baseline and on-study lower GI endoscopy procedures as part of this trial.

Upper GI Endoscopy: The duodenum was evaluated by forward-viewing and/or side-viewing gastroscopes (with still and video documentation with closed and open biopsy forceps near mucosa). All randomized patients with a duodenum had baseline and on-study UGI endoscopy as part of this trial. Subjects stratified to the duodenal group must have duodenal biopsies of all polyps 1 cm or larger to determine HGD and histology required for determining Stage 3 or 4 Spigelman status.

FAP-related primary events by disease site were as follows:
1. Pre-operative, intact colon: Disease progression indicating need for colectomy with IRA or total procto-colectomy
2. Retained rectum or pouch events include one or more of the following:
    a) Excisional intervention by endoscopic snare or trans-anal excision to remove any polyp ≥10 mm in size (per pathology report) and/or pathologic evidence of high grade dysplasia.
    b) Disease progression indicating need for proctectomy or pouch resection
3. Duodenal disease includes the following:
    a) Progression in Spigelman Stage to more advanced stage (Stage 2, 3 or 4)
    b) Disease progression indicating need for excisional intervention (sub-mucosal resection, trans-duodenal excision, ampullectomy, duodenectomy, Whipple procedure)
    c) Development of cancer Disease progression is based on endoscopic evaluations compared to baseline demonstrating a clinically significant increase in number and/or size of polyps (~25% increase in disease burden), presence of a large sessile or ulcerated adenoma not amenable to removal, high grade dysplasia in any adenoma, or in-situ or invasive cancer.

Colonoscopy or flexible sigmoidoscopy were used to assess the colon, rectum or the neo-rectum (ileal pouch) and video images captured for archiving and subsequent review. The last images were retroflexed pictures of the distal rectum or pouch at the anorectal ring. One pass was performed.

The entire residual rectum or pouch was video-captured three times by advancing a flexible scope to ileo-rectal anastomosis or proximal pouch. After advancement, the scope was "twirled" to visualize all walls of the bowel as it is withdrawn. Retroflexed views of the distal rectum were obtained at each visualization.

Duodenal assessment used a forward and/or side-viewing endoscope with video images captured for subsequent review. The Spigelman classification at screening was used to stage the initial extent of disease and assess subject eligibility.

At six month intervals (+/−two weeks), subjects underwent repeat upper and lower endoscopy. At any interval assessment, if any subject had disease progression indicating the need for an excisional intervention, or has duodenal Spigelman stage progression, the subject was considered to have an FAP-related event and will come off study treatment. Video recordings of all procedures and qualitative assessments were compared to the exam 6 months prior. Stratified log-rank analysis was performed to compare time to first FAP-related event between eflornithine/sulindac to each agent alone. FAP-related events were powered to assume (1) a doubling of the two-year event-free proportion from either of the single agents to the combination with power of at least 85% and (b) an expected a two-year event-free proportion of 60% for the combination and 30% in each single agent.

Based primarily on published literature of eflornithine or NSAID effects on polyposis (Keller & Giardiello, 2003), the sample size was calculated as overall event rate of 30% for eflornithine/sulindac therapy and 70% for monotherapy over 2 years, with an 85% power to detect a significant difference between eflornithine/sulindac therapy and monotherapy, which would require 50-55 patients in each arm. The composite primary endpoint, time to first FRE in the combination treatment compared with each drug alone, was analyzed on the intent-to-treat (ITT) population using a 2-sided stratified log-rank test ($\alpha=0.05$) and reported graphically as Kaplan-Meier curves. For the composite primary endpoint, patients lost to follow-up were censored at the time their status was last known. Continuous data were evaluated using an analysis of covariance with main effect of treatment, baseline value, and randomization strata as covariates. Categorical data were analyzed using chi-square tests and Cochran-Mantel Haenszel controlling for randomization strata. Ordered categorical data were analyzed using Kruskal-Wallis nonparametric tests. Safety assessments were made on all patients who received at least 1 dose of study drug without inferential statistics. The primary endpoint Type 1 error control was based on the sequential test approach with the primary comparison being between combination and sulindac. If the primary comparison was statistically significant at the 0.05 significance level, then the test proceeded to the next comparison between the combination and eflornithine.

Figure 2:
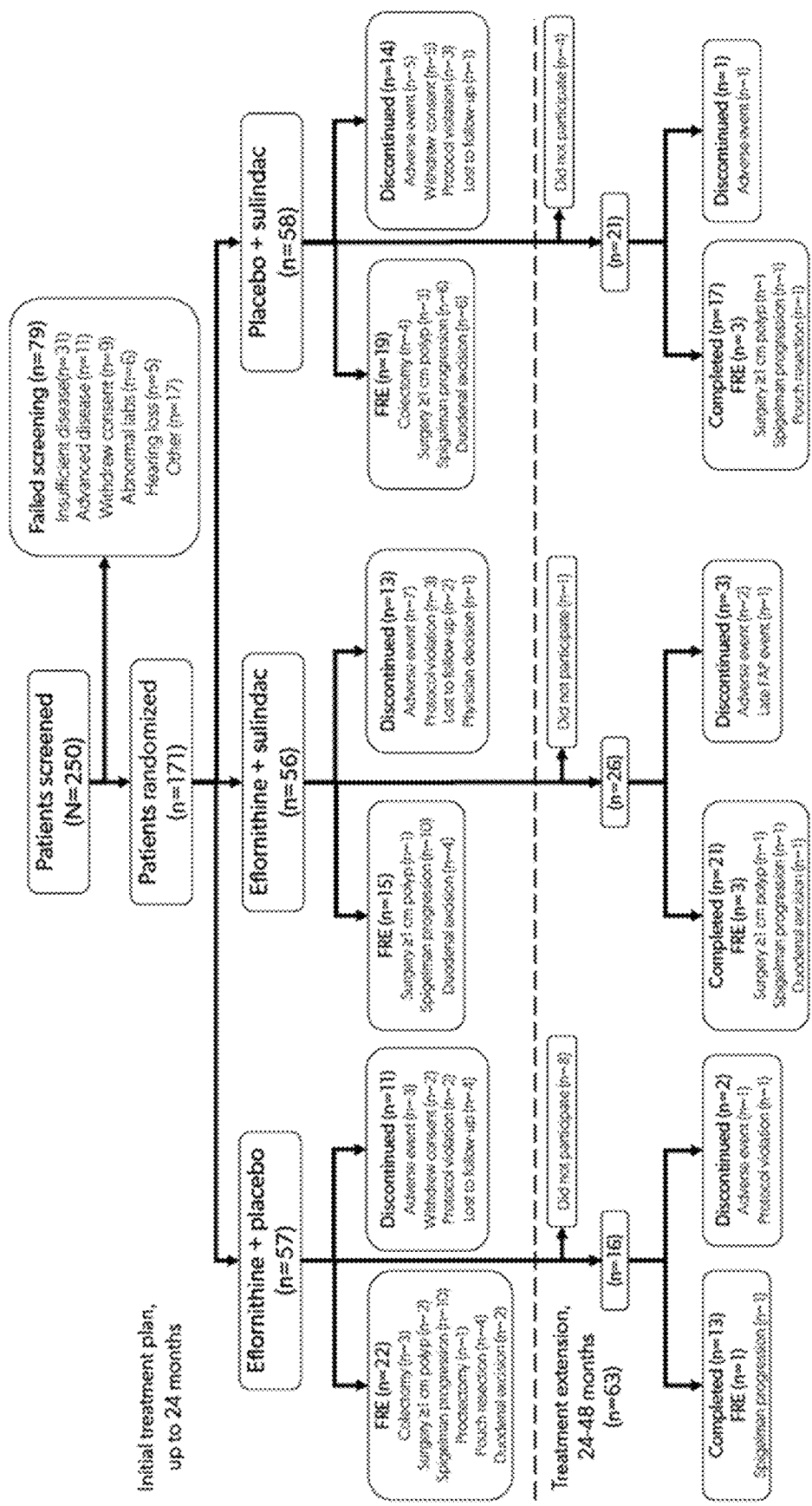
FIG. 2. Study patient disposition. FRE: FAP-related event (need for colectomy, proctocolectomy, duodenal polyp/ampullary excisions, duodenectomy, Whipple procedure, pouch or retained rectum resection, excision of any polyp ≥10 mm in size, or diagnosis of high-grade dysplasia in the rectum or pouch, or duodenal disease progression of ≥1 Spigelman stage).

Two hundred fifty patients were screened, with 171 being randomized for treatment (see FIG. 2). The baseline patient demographics, which were similar across the treatment groups, are shown in Table 1. Safety data are provided in Tables 2-4. There were no differences in safety profiles between the treatment arms. TRAE were reported by 67.9% of patients receiving eflornithine/sulindac, 73.7% of patients receiving sulindac, and 55.4% of patients receiving eflornithine alone (Table 2). Most TRAEs were mild to moderate in severity and resolved with minimal intervention. The most common TRAEs reported were nausea (15.4%), headache (10.7%), diarrhea (7.1%), vomiting (6.5%), rectal hemorrhage (6.5%), abdominal pain (6.5%), flatulence (5.9%), dyspepsia (5.3%), and decreased appetite (5.3%). Serious TRAEs reported included 1 patient each for the following: acute pancreatitis, nephritis, and psychosis/paranoia (eflornithine/sulindac); severe nausea, deep vein thrombosis, worsening of depression, and spontaneous abortion (sulindac); and stroke (eflornithine). Discontinuations due to AEs were reported for 9 (16.1%) patients receiving eflornithine/sulindac, 6 (10.3%) patients receiving sulindac, and 5 (8.8%) patients receiving eflornithine.

TABLE 1

Baseline patient demographics and disease characteristics (mean (SD), unless otherwise stated) of the ITT population

| Characteristic | Eflornithine/sulindac (N = 56) | Sulindac (N = 58) | Eflornithine (N = 57) | Total (N = 171) |
|---|---|---|---|---|
| Male, n (%) | 34 (60.7) | 37 (63.8) | 28 (49.1) | 99 (57.9) |
| Age, y | 37.8 (13.4) | 38.1 (13.7) | 39.7 (14.8) | 38.5 (13.9) |
| Age by FAP stratification, y | | | | |
| Pre-colectomy | 27.4 (9.7) | 22.5 (3.7) | 23.2 (8.7) | 24.3 (7.8) |
| Rectal-pouch polyposis | 38.2 (11.6) | 35.3 (11.7) | 42.4 (14.1) | 38.7 (12.5) |
| Duodenal disease | 41.5 (13.3) | 44.9 (11.4) | 44.7 (12.5) | 43.7 (12.4) |
| Race, n (%) | | | | |
| White | 48 (85.7) | 50 (86.2) | 54 (94.7) | 152 (88.9) |
| Black | 6 (10.7) | 3 (5.2) | 1 (1.8) | 10 (5.8) |
| Other | 2 (3.6) | 5 (8.6) | 2 (3.5) | 9 (5.3) |
| BMI, kg/m$^2$ | 27.2 (5.9) | 27.2 (5.4) | 28.4 (7.7) | 27.6 (6.4) |
| Time since diagnosis, y | 17.4 (10.4) | 15.5 (11.4) | 19.7 (11.5) | 17.5 (11.2) |
| Surgical status, n (%) | | | | |
| Pre-colectomy | 13 (23.2) | 13 (22.4) | 12 (21.1) | 38 (22.2) |
| Colectomy with ileorectal anastomosis (IRA) | 13 (23.2) | 19 (32.8) | 21 (36.8) | 53 (31.0) |
| Proctocolectomy with ileal pouch anal anastomosis (IPAA) | 28 (50.0) | 21 (36.2) | 18 (31.6) | 67 (39.2) |

TABLE 1-continued

Baseline patient demographics and disease characteristics (mean (SD), unless otherwise stated) of the ITT population

| Characteristic | Eflornithine/ sulindac (N = 56) | Sulindac (N = 58) | Eflornithine (N = 57) | Total (N = 171) |
|---|---|---|---|---|
| Colectomy with ileostomy | 2 (3.6) | 5 (8.6) | 6 (10.5) | 13 (7.6) |

TABLE 2

Safety data

| Characteristic | Eflornithine/ sulindac (N = 56) | Sulindac (N = 57) | Eflornithine (N = 56) | Total (N = 169) |
|---|---|---|---|---|
| Number of patients reporting TEAEs, n (%) | 52 (92.9) | 50 (87.7) | 49 (87.5) | 151 (89.3) |
| Number of patients reporting TRAEs, n (%) | 38 (67.9) | 42 (73.7) | 31 (55.4) | 111 (65.7) |
| Number of patients reporting TEAEs ≥ Grade 3, n (%) | 12 (21.4) | 12 (21.1) | 17 (30.4) | 41 (24.3) |
| Number of patients reporting TRSAEs, n (%) | 3 (5.4) | 4 (7.0) | 1 (1.8) | 8 (4.7) |
| Number of patients discontinuing due to a TRAE, n (%) | 7 (12.5) | 5 (8.8) | 3 (5.4) | 15 (8.8) |
| Death, n (%) | 0 | 0 | 0 | 0 |
| Number of patients reporting following TRAEs, n (%) | | | | |
| Nausea | 9 (16.1) | 9 (15.8) | 8 (14.3) | 26 (15.4) |
| Headache | 3 (5.4) | 7 (12.3) | 8 (14.3) | 18 (10.7) |
| Diarrhea | 4 (7.1) | 3 (5.3) | 5 (8.9) | 12 (7.1) |
| Vomiting | 2 (3.6) | 4 (7.0) | 5 (8.9) | 11 (6.5) |
| Rectal hemorrhage | 4 (7.1) | 4 (7.0) | 3 (5.4) | 11 (6.5) |
| Abdominal pain | 3 (5.4) | 4 (7.0) | 4 (7.1) | 11 (6.5) |
| Flatulence | 4 (7.1) | 3 (5.3) | 3 (5.4) | 10 (5.9) |
| Dyspepsia | 2 (3.6) | 4 (7.0) | 3 (5.4) | 9 (5.3) |
| Decreased appetite | 2 (3.6) | 4 (7.0) | 3 (5.4) | 9 (5.3) |
| Abdominal distension | 1 (1.8) | 3 (5.3) | 4 (7.1) | 8 (4.7) |
| Fatigue | 1 (1.8) | 4 (7.0) | 3 (5.4) | 8 (4.7) |
| Hematochezia | 2 (3.6) | 2 (3.5) | 4 (7.1) | 8 (4.7) |
| Upper abdominal pain | 5 (8.9) | 1 (1.8) | 2 (3.6) | 8 (4.7) |
| Dizziness | 2 (3.6) | 2 (3.5) | 3 (5.4) | 7 (4.1) |
| Tinnitus | 1 (1.8) | 5 (8.8) | 1 (1.8) | 7 (4.1) |
| Pruritus | 1 (1.8) | 4 (7.0) | 2 (3.6) | 7 (4.1) |
| Rash | 6 (10.7) | 0 | 0 | 6 (3.6) |
| Alopecia | 2 (3.6) | 3 (5.3) | 0 | 5 (3.0) |
| Thrombocytopenia | 0 | 3 (5.3) | 1 (1.8) | 4 (2.4) |
| Depression | 0 | 3 (5.3) | 1 (1.8) | 4 (2.4) |
| Frequent bowel movements | 0 | 1 (1.8) | 3 (5.4) | 4 (2.4) |
| Gastritis erosive | 3 (5.4) | 0 | 0 | 3 (1.8) |

AE, adverse event;
TEAE, treatment-emergent AE;
TRAE, treatment-related AE;
TRSAE, treatment-related serious AE

TABLE 3

Treatment-related serious adverse events

| CPP-1X/sulindac | CPP-1X | Sulindac |
|---|---|---|
| Acute Pancreatitis Possible Nephritis Psychosis and Paranoia | Stroke | Severe Nausea Deep Vein Thrombosis Worsening of Depression Spontaneous Abortion |

TABLE 4

Treatment-related hearing adverse events

| | CPP-1X/sulindac | CPP-1X | Sulindac |
|---|---|---|---|
| Hearing loss N | 3 | 1 | 2 |
| Tinnitus N | 1 | 1 | 5 |

The composite primary efficacy endpoint was time to first prespecified FAP-related event (FRE) as an indication of disease progression, with the following possible events: (a) the need for colectomy, proctocolectomy, duodenal polyp/ ampullary excisions, duodenectomy, Whipple procedure, or the need for pouch or retained rectum resection); (b) excision of any polyp ≥10 mm in size, (c) diagnosis of high-grade dysplasia in the rectum or pouch; (d) duodenal disease progression of Spigelman stage, excluding stage 0 to 1. A secondary efficacy endpoint was time to first FRE in each of the stratification groups. Patients were monitored for adverse events (AEs) and serious AEs (SAEs) which were reported in accordance with National Cancer Institute's Common Terminology Criteria for Adverse Events (CT-CAE) Version 4.0 (CTCAE, 2010). Treatment-emergent AE (TEAE) were defined as any AE occurring after administration of the first dose of study drug and through 30 days after the last dose of study drug. Treatment-related AE (TRAE) were defined as any AE that were considered possibly, probably, or definitely related to study drug. Laboratory results were monitored to detect any safety signals.

Figure 3:
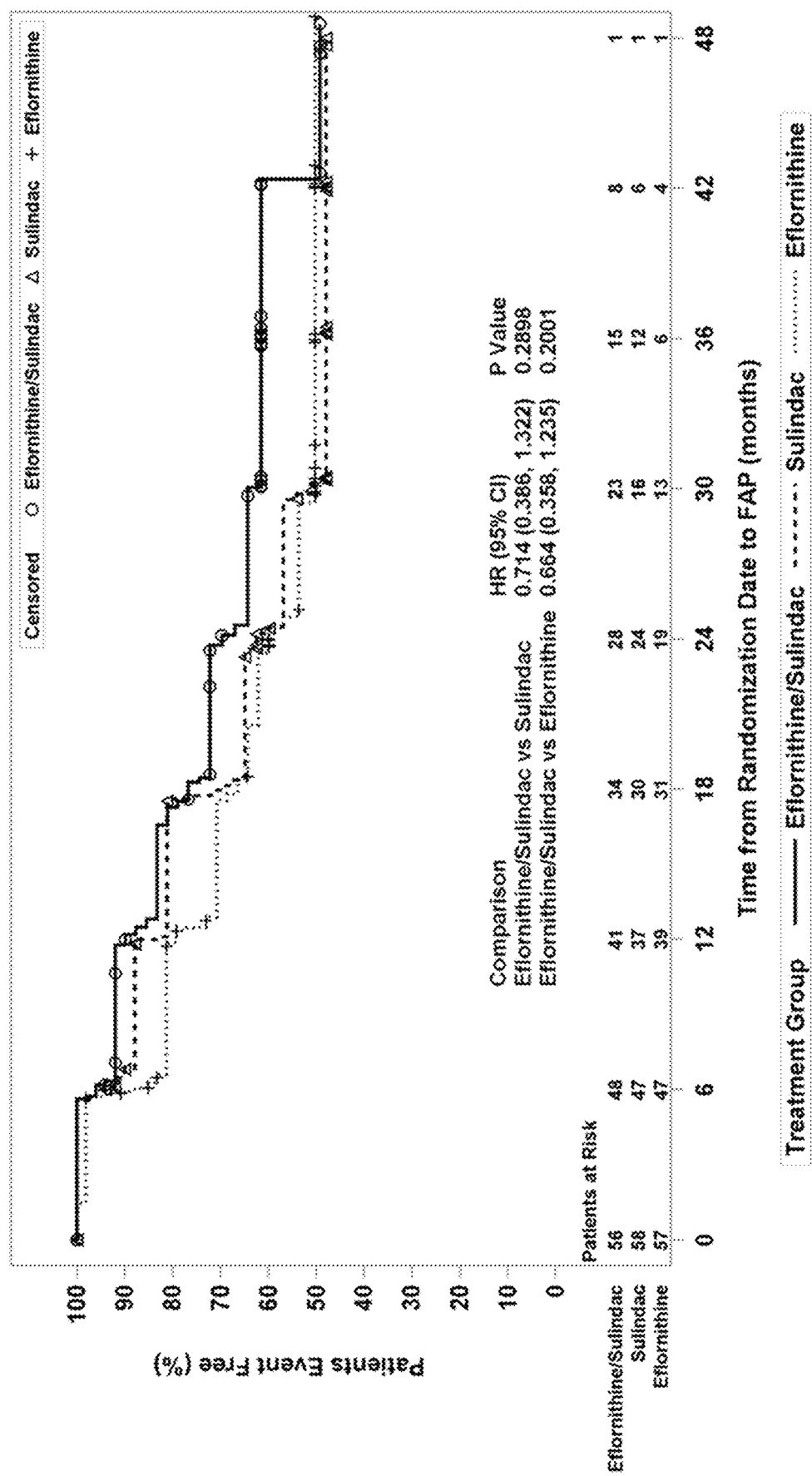
FIG. 3. Kaplan-Meier curves for time to first FRE by treatment arm in the total ITT study population.

The percent of subjects that were event free over the course of the study is shown in FIG. 3. Taking the entire population of patients treated with the combination of eflornithine and sulindac regardless of stratification, the combination therapy did not provide a statistically significant improvement over either single agent treatment. No difference in time to FAP-related events between eflornithine/ sulindac compares to each single agent alone was observed. Most FAP-related events occurred in less than or equal to 24 months. Furthermore, adverse events and SAEs in the combination treatment were comparable to single agents. Notably, all of the surgically related FAP-related events that occurred in the combination therapy group occurred in the duodenal anatomy (Table 5)-no subject in the combination arm had disease progression indicating the need for colectomy, pouch resection, or proctectomy.

TABLE 5

Surgical FAP-related events by disease site

| Type | Combo | CPP-1X | Sulindac |
|---|---|---|---|
| Colon | (N = 12) | (N = 13) | (N = 13) |
| Disease progression | 0 | 3 | 4 |
| Colectomy | 0 | 0 | 2 |
| Event-free proportion | 100% | 76.9% | 69.2% |
| Rectum and Pouch | (N = 41) | (N = 39) | (N = 40) |
| Disease progression | 0 | 5 | 2 |
| Proctectomy/pouch resection | 0 | 1 | 1 |
| Event-free proportion | 100% | 87.2% | 95% |
| Duodenum | N = 54 | N = 55 | N = 57 |
| Disease progression | 6 | 3 | 10 |
| Excisional intervention | 5 | 3 | 6 |
| Spigelman stage progression | 11 | 12 | 7 |
| Event-free proportion | 68.5% | 72.7% | 70.2% |

Composite primary endpoint: Cumulatively, FREs occurred in 18/56 (32.1%), 22/58 (37.9%), and 23/57 (40.4%) corresponding to event-free rates of 67.9%, 63.1%, and 59.6% in patients receiving combination, sulindac, or eflornithine, respectively. Kaplan-Meier estimated mean times to first FRE in the ITT population were 32.3 months, 23.6 months, and 21.8 months for patients receiving combination, sulindac, or eflornithine, respectively, corresponding to risk reductions for FRE of 29% (HR=0.714, 95% CI: 0.386-1.322; p=0.280) for combination versus sulindac and 33% (HR=0.664; 95% CI: 0.358-1.235; p=0.200) for combination versus eflornithine (FIG. 3). The differences in time to first FRE were not significant.

No study patient developed cancer in the duodenum, colorectum, retained rectum, or pouch during the study. Fourteen patients with duodenal polyposis progression underwent duodenal excisional procedures (eflornithine/sulindac: 5; sulindac: 6; eflornithine: 3). Twelve patients had progression of lower gastrointestinal polyposis (eflornithine/sulindac: 2 polypectomies (≥10 mm in size and/or high grade dysplasia); sulindac: 3 surgeries, 4 polypectomies; eflornithine: 1 surgery, 2 polypectomies). Disease progression in the duodenum included Spigelman stage progression (n=30) and need for duodenal endoscopic excisional intervention (n=19). Only 8/30 patients with Spigelman stage progression underwent intervention for disease progression or had an additional FRE, whereas the remaining 22 patients did not exhibit disease progression significant enough to require intervention.

Figure 6A:
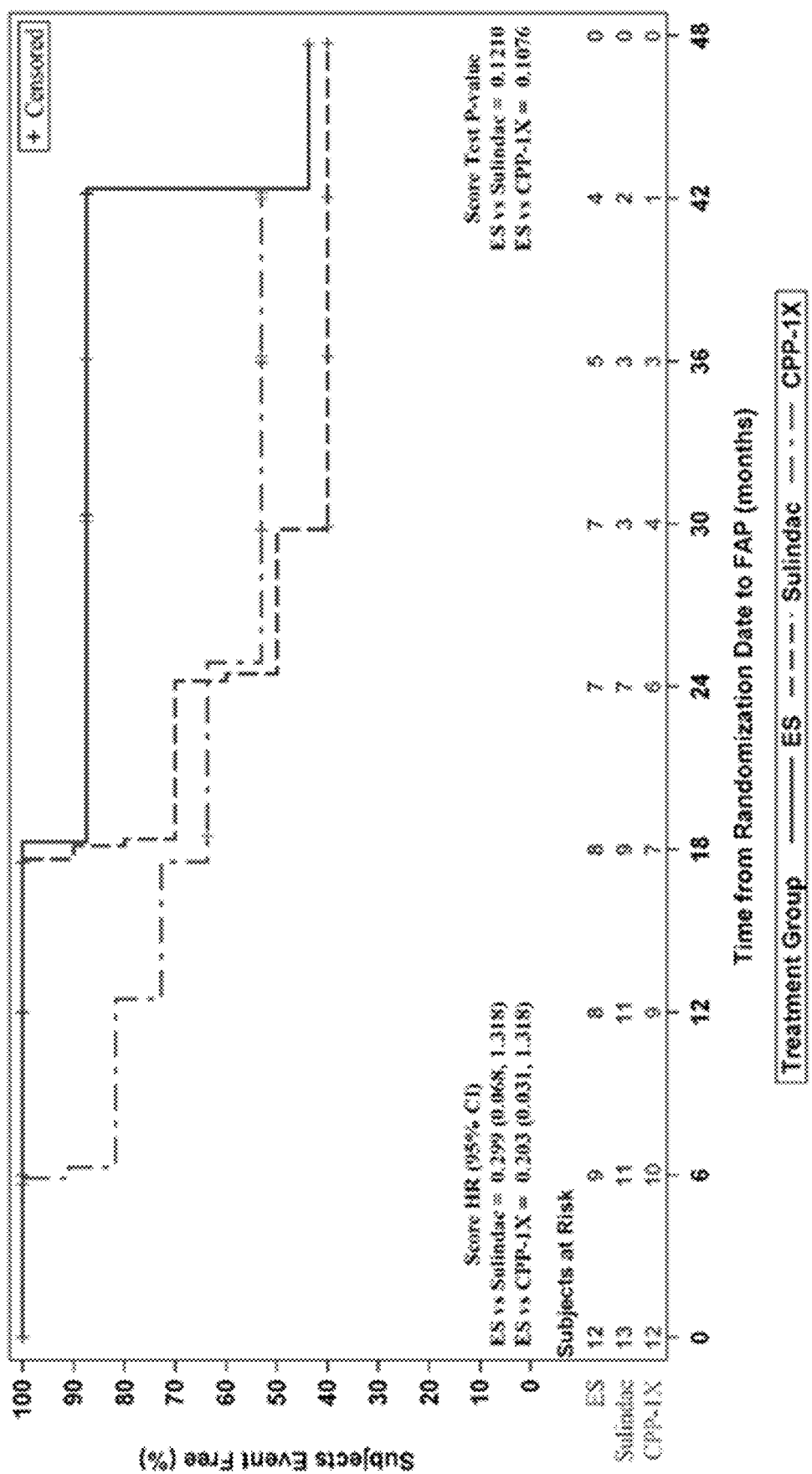
FIGS. 6A-6C. Kaplan-Meier curves in the ITT population for time to first FRE by treatment arm (A) pre-colectomy stratum, (B) post-colectomy with rectal or ileal pouch polyposis stratum, and (C) duodenal polyposis stratum.
Figure 6B:
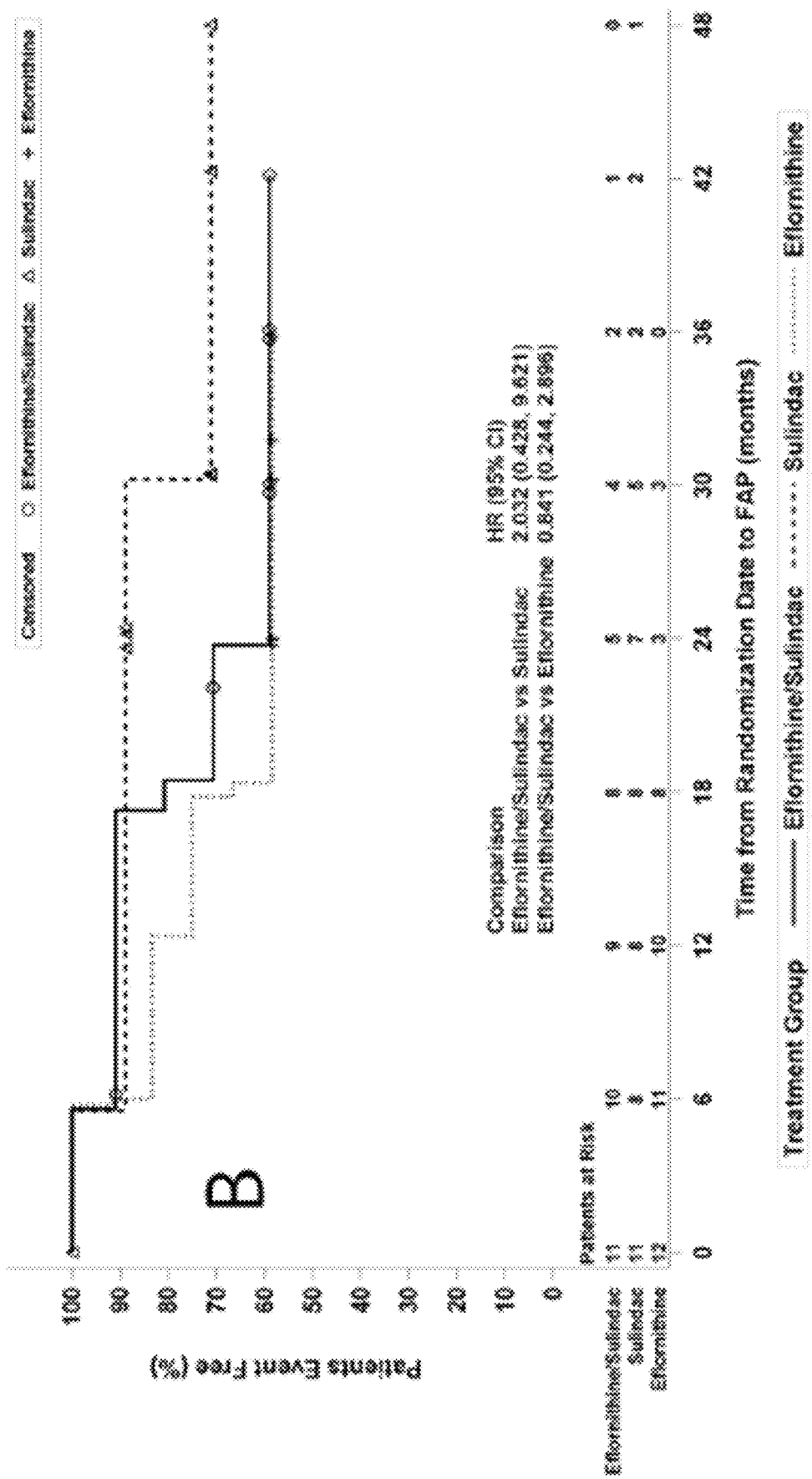
Figure 6C:
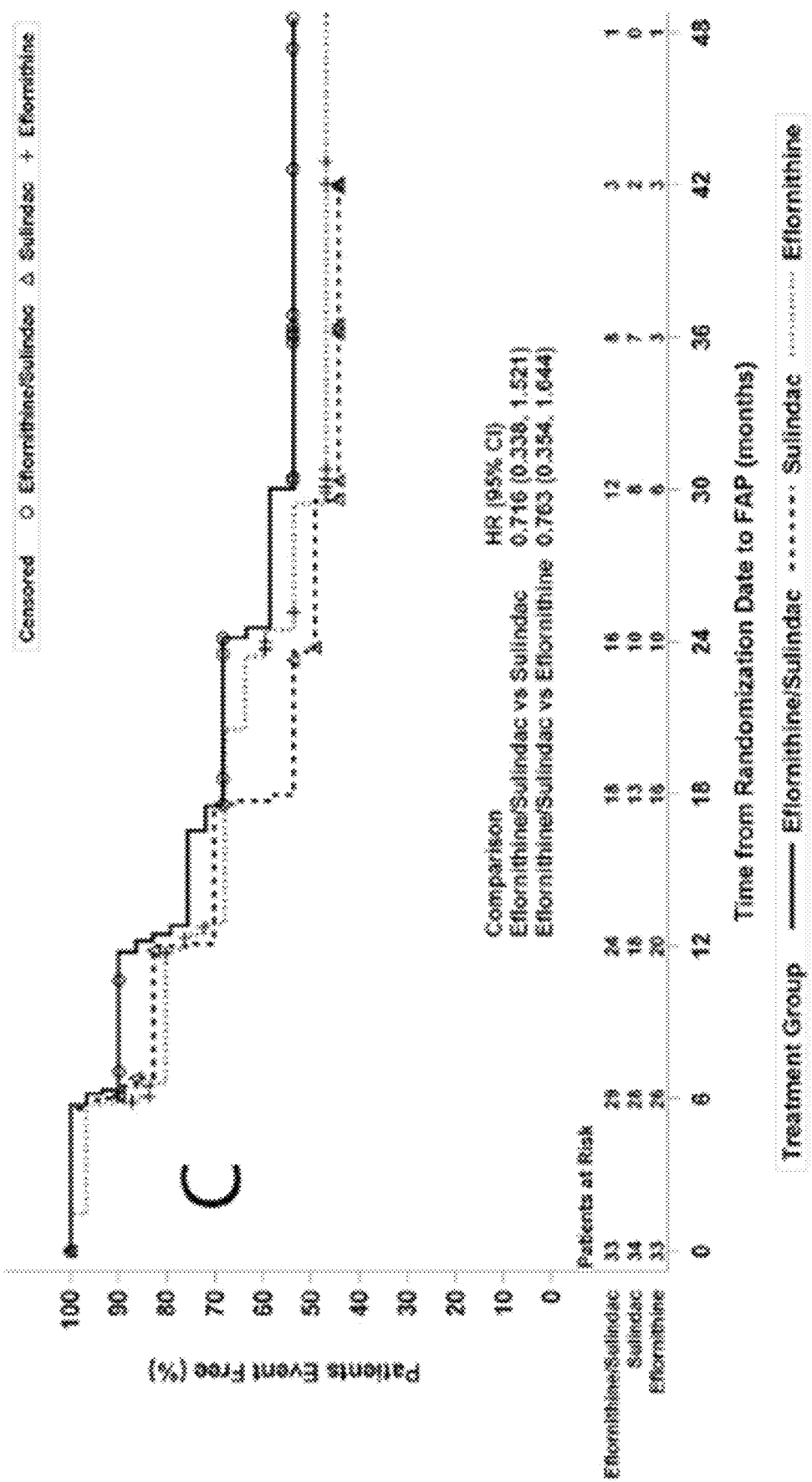

Secondary endpoint: Efficacy results for all three strata are given in Table 6. FREs occurred in 2/12 (16.7%), 6/13 (46.2%), and 5/12 (41.7%) of pre-colectomy patients in the combination, sulindac, and eflornithine arms, respectively. There were no polyposis events or surgeries in the lower gastrointestinal tract among patients receiving combination therapy in this stratum. Details of all FREs by stratum and treatment arm are given in Table 7. Kaplan-Meier estimated mean time to first FRE was 39.3 months in the combination arm (FIG. 6A) versus 25.2 months in the sulindac arm (risk reduction for FRE of 70%; HR=0.299; 95% CI: 0.068, 1.318) and 19.7 months in the eflornithine arm (risk reductions for FRE of 80%; HR=0.203; 95% CI: 0.031, 1.318). In the post-colectomy with rectal/ileal pouch polyposis stratum, FREs occurred in 4/11 (36.4%), 2/11(18.2%), and 5/12 (41.7%) patients in the combination, sulindac, and eflornithine arms, respectively. For this stratum, InSiGHT stage was not used as a criterion for assignment to treatment resulting in the combination arm having a higher proportion InSiGHT stage 3 patients than either monotherapy arm. Kaplan-Meier estimated mean times to first FRE were 20.9 months, 27.5 months, and 15.7 months for patients receiving combination, sulindac, or eflornithine, respectively, corresponding to risk reduction for FRE of 16% (HR=0.841; 95% CI: 0.244, 2.896) between combination and eflornithine arms (FIG. 6B). There was no risk reduction between combination and sulindac arms, HR=2.032 (95% CI: 0.428, 9.621). In the duodenal polyposis stratum, FREs occurred in 13/33 (39.4%), 14/34(41.2%), and 13/33 (39.4%) patients in the combination, sulindac, and eflornithine arms, respectively. Kaplan-Meier estimated mean time to first FRE was 23.6 months in the combination arm (FIG. 6C) versus 21.1 months in the sulindac arm (risk reduction for FRE of 29%; HR=0.716; 95% CI: 0.338, 1.521) and 21.7 months in the eflornithine arm (risk reduction for FRE of 24%; HR=0.763; 95% CI: 0.354, 1.644). The status of all secondary endpoint evaluations is given in Table 8.

TABLE 6

Efficacy results by stratum and treatment arm

| | Eflornithine/Sulindac | Sulindac | Eflornithine |
|---|---|---|---|
| Pre-colectomy stratum, N | 12 | 13 | 12 |
| Patients with FRE, n (%) | 2 (16.7) | 6 (46.2) | 5 (41.7) |
| Mean time to first FRE, months | 39.3 | 25.2 | 19.7 |
| Risk reduction versus combination, % | | 70 | 80 |
| Hazard ratio (95% CI) | | 0.299 (0.068, 1.318) | 0.203 (0.031, 1.318) |
| Post-colectomy, rectal/ileal pouch stratum, N | 11 | 11 | 12 |
| Patients with FRE, n (%) | 4 (36.4) | 2 (18.2) | 5 (41.7) |
| Mean time to first FRE, months | 20.9 | 27.5 | 15.7 |
| Risk reduction versus combination | | 16 | None |
| Hazard ratio (95% CI) | | 0.841 (0.244, 2.896) | 2.032 (0.428, 9.621) |
| Duodenal polyposis stratum, N | 33 | 34 | 33 |
| Patients with FRE, n (%) | 12 (36.4) | 14 (41.2) | 13 (39.4) |
| Mean time to first FRE, months | 23.6 | 21.1 | 21.7 |
| Risk reduction versus combination | | 29 | 24 |
| Hazard ratio (95% CI) | | 0.716 (0.338, 1.521) | 0.763 (0.354, 1.644) |

CI, confidence interval;
FAP, familial adenomatous polyposis;
FRE, FAP-related event

TABLE 7

FREs by stratum and treatment arm

| FRE type | Eflornithine/Sulindac | Sulindac | Eflornithine |
|---|---|---|---|
| Pre-colectomy stratum, total FRE | 2 | 6 | 5 |
| Spigelman stage progression | 2 | 1 | 2 |
| Colectomy | | 4 | 2 |
| Colectomy and Spigelman stage progression | | | 1 |
| Duodenal excision and Spigelman stage progression | | 1 | |

TABLE 7-continued

FREs by stratum and treatment arm

| FRE type | Eflornithine/Sulindac | Sulindac | Eflornithine |
|---|---|---|---|
| Post-colectomy, rectal/ileal pouch stratum, total FRE | 4 | 2 | 5 |
| Spigelman stage progression | 3 | | 1 |
| Pouch resection | | 1 | 2 |
| ≥10 mm polyp removed in rectum/pouch | | 1 | 1 |
| Proctocolectomy | | | 1 |
| Duodenal excision | 1 | | |
| Duodenal polyposis stratum, total FRE | 12 | 14 | 13 |
| Spigelman stage progression | 5 | 3 | 7 |
| Duodenal excision | 4 | 6 | 2 |
| Duodenal excision and Spigelman stage progression | 1 | 2 | 1 |
| Duodenal excision and ≥ 10 mm polyp removed in rectum/pouch | | 1 | |
| ≥10 mm polyp removed in rectum/pouch | 2 | 1 | 1 |
| Proctocolectomy and ≥ 10 mm polyp removed in rectum/pouch | | 1 | |
| Pouch resection | | | 2 |

FAP, familial adenomatous polyposis;
FRE, FAP-related event

TABLE 8

Status of secondary endpoints

| Endpoint | Status |
|---|---|
| Time to first FAP-related event in prespecified strata | Included in manuscript |
| Ototoxicity | Analysis in progress |
| Cardiotoxicity | Analysis in progress |
| Ornithine decarboxylase polymorphism | Analysis in progress |
| Excretion of urinary polyamines | Analysis in progress |
| Tissue and dietary polyamines | Analysis in progress |
| Population pharmacokinetics | Analysis in progress |
| Health-related quality of life | Analysis in progress |
| Endoscopy video analysis | Analysis to be initiated |
| Pharmacogenetic analysis | Analysis to be initiated |
| Genetic analysis | Analysis to be initiated |

Figure 4:
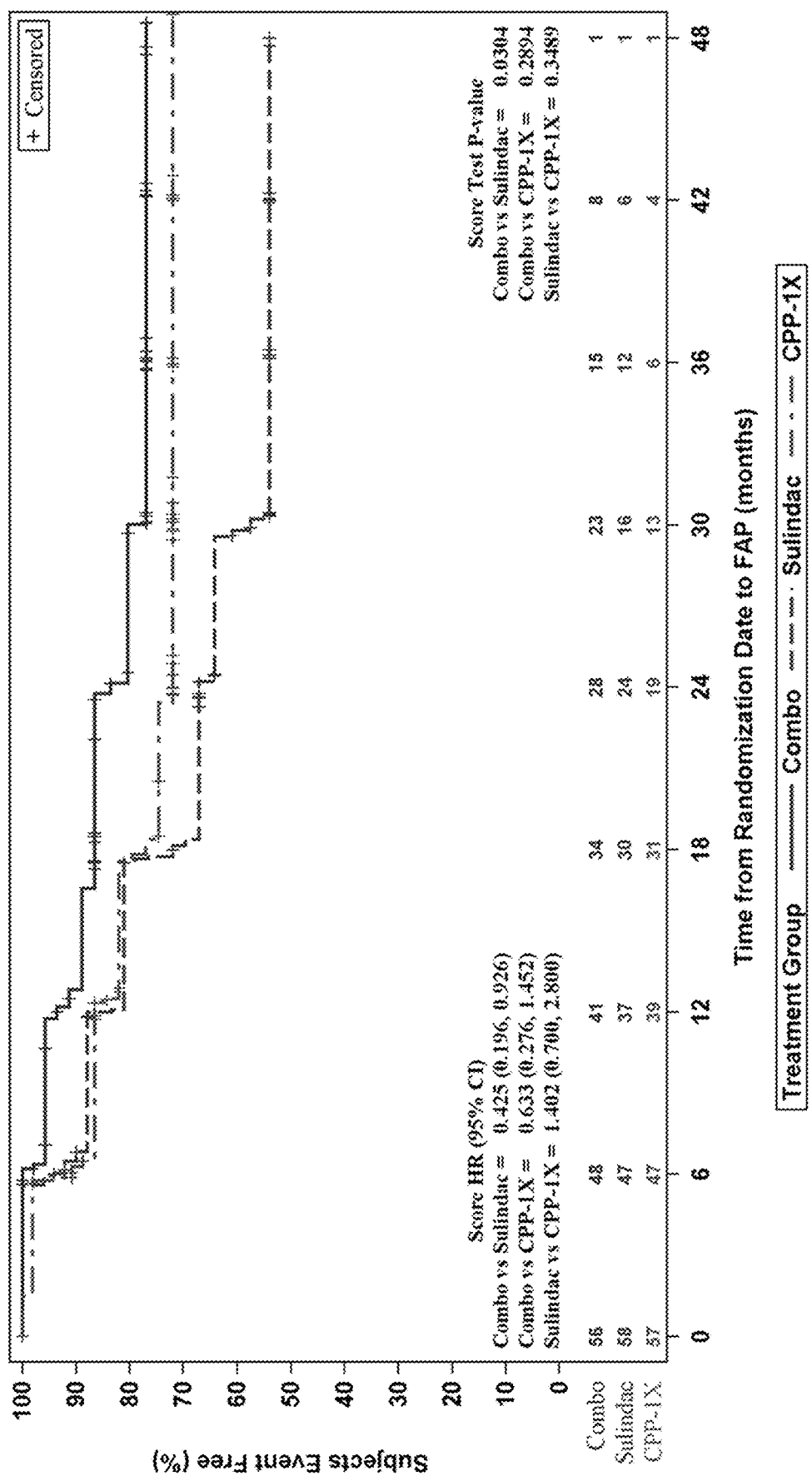
FIG. 4. Post-hoc analysis of time to first FAP-related event with 22 patients censored for Spigelman stage progression without duodenal endoscopic or surgical intervention.
Figure 5:
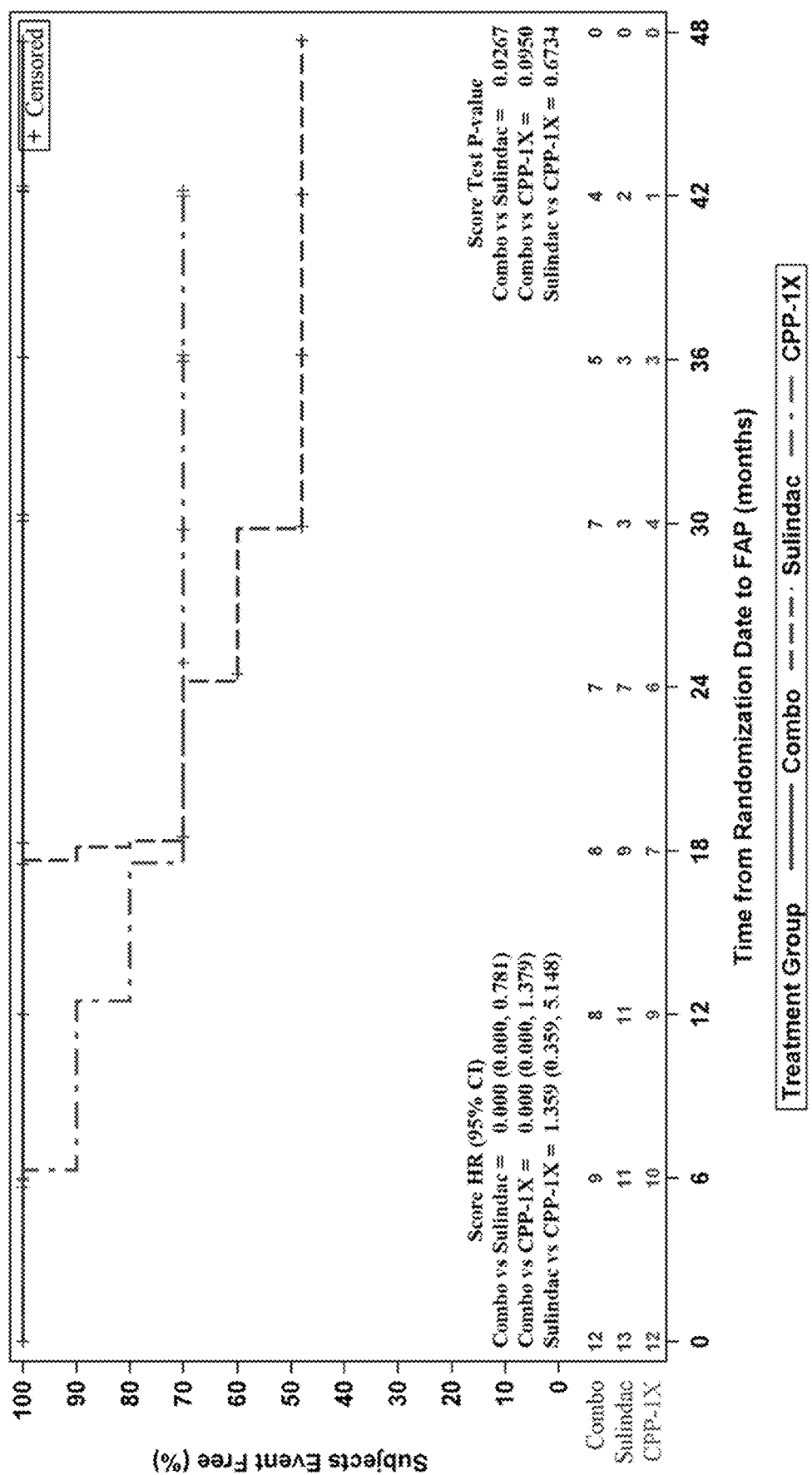
FIG. 5. Post-hoc analysis of time to first FAP-related event for the colon/pre-colectomy stratified subjects with 5 patients censored for Spigelman stage progression without duodenal endoscopic or surgical intervention.
Figure 7:
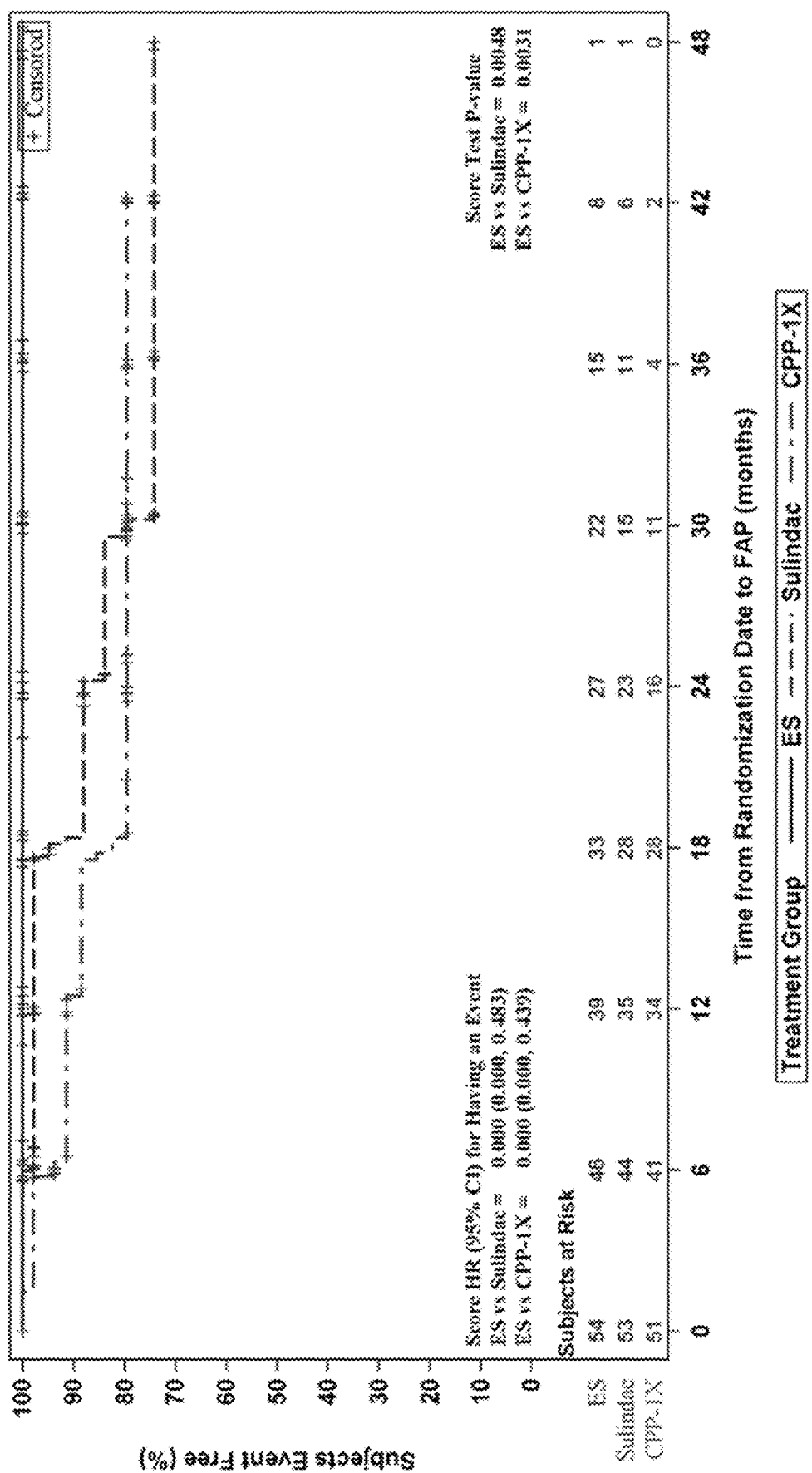
FIG. 7. Kaplan-Meier curves for subjects with lower GI anatomy for delay in lower GI surgery events.
Figure 8:
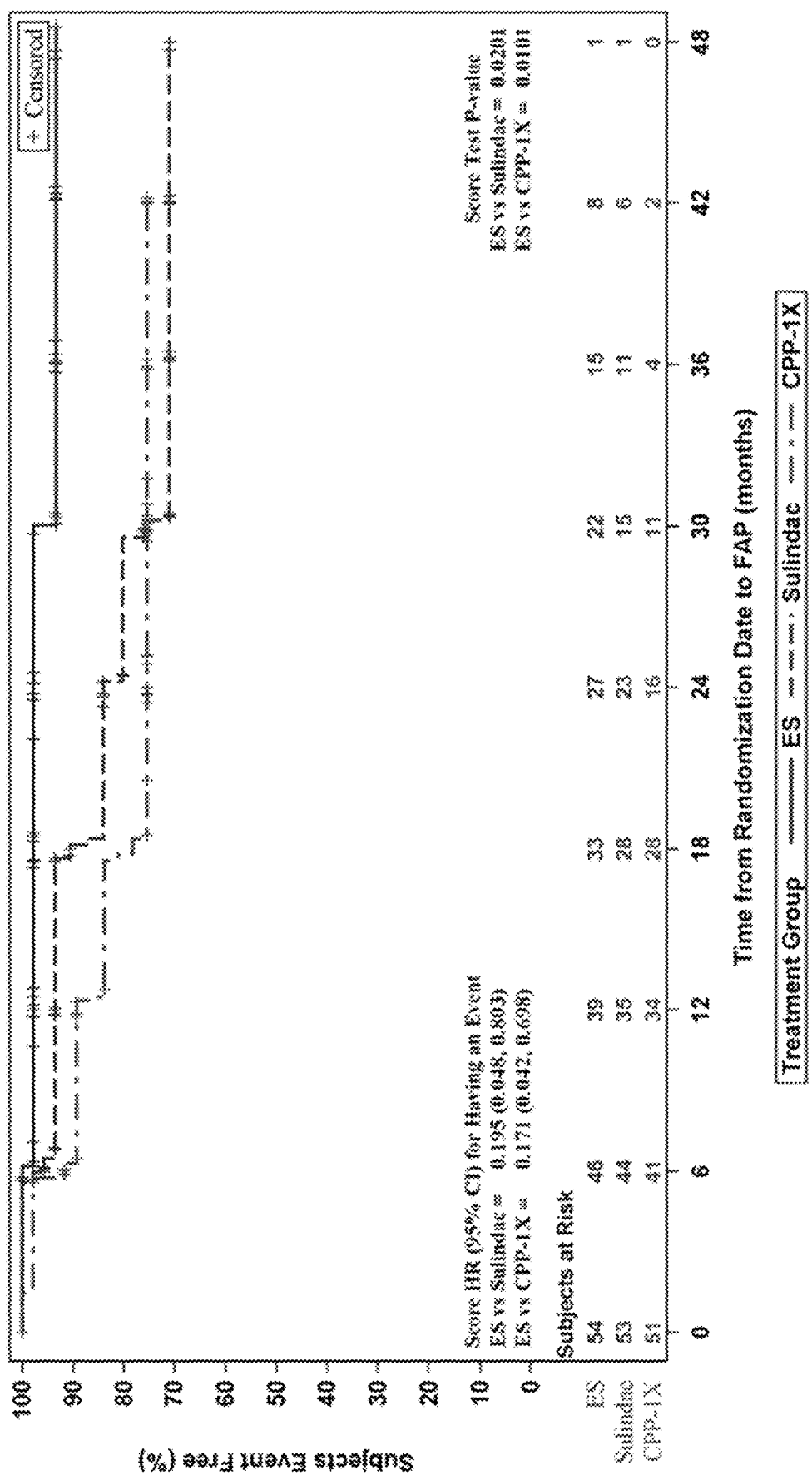
FIG. 8. Kaplan-Meier curves for subjects with lower GI anatomy for delay in lower GI surgery and high-risk polyp removal events.

The majority of FAP-related events occurred in the duodenum, with 35% being due to Spigelman stage progression only. While Spigelman stage progression without excisional procedure was included in the composite endpoint of the study, this endpoint is now recognized to have little clinical importance. This is because while Spigelman staging is of value in defining eligibility, without a subsequent endoscopic/surgical procedure, it is not a reliable endpoint (Buglow, 2004; Thiruvengadam, 2019; Tierney, 2017). Twenty-two subjects had this primary end-point only. As such, post-hoc analyses of the trial data were performed after censoring these subjects. These data, shown in FIG. 4, show that the combination of eflornithine and sulindac resulted in a statistically significantly lower number of event-free subjects at completion of the trial. This effect was even further enhanced for the colon/pre-colectomy subjects (FIG. 5). In addition, in evaluating need for surgery in the lower GI, no disease progression indicating need for surgery occurred in the lower GI for patients receiving the combination of eflornithine and sulindac (Table 9; FIG. 7). Furthermore, a statistically significant decrease in both surgeries and high-risk polyp resection in the lower GI was seen for patients receiving the combination of eflornithine and sulindac (FIG. 8). As such, the administration of eflornithine and sulindac to patients with FAP and having at least a partially intact lower GI tract provides a major delay in polyposis progression.

TABLE 9

Lower GI surgery events in subject with lower GI anatomy
Event Rate Distribution of FAP-related Surgery Events in Lower GI

| Surgery Events | Combo (N = 56) | CPP-1X (N = 57) | Sulindac (N = 58) | Overall (N = 171) |
|---|---|---|---|---|
| Need colectomy | 0 | 3 | 4 | 7 |
| Need proctectomy | 0 | 1 | 1 | 2 |
| Need pouch resection | 0 | 4 | 1 | 5 |
| Total Surgical Events | 0 | 8 | 6 | 14 |
| Event Rate | 0/56 (0%) | 8/57 (14%) | 6/58 (10%) | |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,647,858
U.S. Pat. No. 3,654,349
U.S. Pat. No. 4,330,559
U.S. Pat. No. 4,413,141
U.S. Pat. No. 5,814,625
U.S. Pat. No. 5,843,929
U.S. Pat. No. 6,258,845
U.S. Pat. No. 6,428,809
U.S. Pat. No. 6,702,683
U.S. Pat. No. 8,329,636
U.S. Pat. No. 9,121,852
U.S. Patent Publication US2013/0217743
U.S. Patent Publication US2015/0301060
PCT Patent Publication WO2014/070767
PCT Patent Publication WO2015/195120
PCT Patent Publication WO2017/075576
Alberts et al., *J. Cell. Biochem. Supp.*, (22):18-23, 1995.
Altman A M, Hui J Y C, Tuttle T M. Quality-of-life implications of risk-reducing cancer surgery. Br J Surg 2018; 105:e121-e30.
AMA Drug Evaluations Annual, 1814-1815, 1994.
Andrews L, Mireskandari S, Jessen J, et al. Impact of familial adenomatous polyposis on young adults: quality of life outcomes. Dis Colon Rectum 2007; 50:1306-15.
Aretz S, Uhlhaas S, Caspari R, et al. Frequency and parental origin of de novo APC mutations in familial adenomatous polyposis. Eur J Hum Genet 2004; 12:52-8.

Bailey et al., *Cancer Prev Res (Phila)* 3, 35-47, 2010.
Barry et al., *J. Natl. Cancer Inst.,* 98(20):1494-500, 2006.
Bedi et al., *Cancer Res.,* 55(9):1811-1816, 1995.
Bellofernandez et al., *Proc. Natl. Acad. Sci. USA,* 90:7804-8, 1993.
Bertagnolli M M, Eagle C J, Zauber A G, et al. Celecoxib for the Prevention of Sporadic Colorectal Adenomas. New Engl J Med 2006; 355:873-84.
Bulow, *Ugeskr Laeger,* 166:2668-2670, 2004.
Bülow S, Björk J, Christensen I J, et al. Duodenal adenomatosis in familial adenomatous polyposis. Gut 2004; 53:381-6.
Burke C A, Dekker E, Samadder N J, Stoffel E, Cohen A. Efficacy and safety of eflornithine (CPP-1X)/sulindac combination therapy versus each as monotherapy in patients with familial adenomatous polyposis (FAP): design and rationale of a randomized, double-blind, Phase III trial. BMC Gastroenterol 2016; 16:87.
Burke C A, Phillips R, Berger M, et al. Children's International Polyposis (CHIP) study: a randomized, double-blind, placebo-controlled study of celecoxib in children with familial adenomatous polyposis. Clin Exp Gastroenterol 2017; 10:1-9.
Burn J, Bishop D T, Chapman P D, et al. A randomized placebo-controlled prevention trial of aspirin and/or resistant starch in young people with familial adenomatous polyposis. Cancer Prev Res (Phila) 2011; 4:655-65.
Campos F G. Surgical treatment of familial adenomatous polyposis: dilemmas and current recommendations. World J Gastroenterol 2014; 20:16620-9.
Childs et al., *Cell. Molec. Life Sci.,* 60:1394-1406, 2003.
Church, Dis. *Colon Rectum,* 48:1708-1713, 2005.
Common Terminology Criteria for Adverse Events (CTCAE) v4.0. National Institutes of Health, 2010. (Accessed Jan. 15, 2019, available at ctep.cancer.gov/protocolDevelopment/electronic_applications/ctc.htm#ctc_40.)
Cruz-Correa M, Hylind L M, Romans K E, Booker S V, Giardiello F M. Long-term treatment with sulindac in familial adenomatous polyposis: A prospective cohort study. Gastroenterology 2002; 122:641-5.
Delker D A, Wood A C, Snow A K, et al. Chemoprevention with Cyclooxygenase and Epidermal Growth Factor Receptor Inhibitors in Familial Adenomatous Polyposis Patients: mRNA Signatures of Duodenal Neoplasia. Cancer Prev Res (Phila) 2018; 11:4-15.
Dozois R R, Kelly K A, Welling D R, et al. Ileal pouch-anal anastomosis: comparison of results in familial adenomatous polyposis and chronic ulcerative colitis. Ann Surg 1989; 210:268-71.
DuBois et al., *Cancer Res.,* 56:733-737, 1996.
Eisinger A L, Nadauld L D, Shelton D N, et al. The adenomatous polyposis coli tumor suppressor gene regulates expression of cyclooxygenase-2 by a mechanism that involves retinoic acid. J Biol Chem 2006; 281:20474-82.
Erdman et al., *Carcinogenesis,* 20:1709-13, 1999.
European Pharmacopoeia, Strasbourg: Council of Europe, 8$^{th}$ Ed., 2014.
Fultz K E, Gerner E W. APC-dependent regulation of ornithine decarboxylase in human colon tumor cells. Mol Carcinog 2002; 34:10-8.
Gerhardt, *Pharmaceutical Processes,* 13(1), 2009.
Gerner et al., *Cancer Epidemoil. Biomarkers Prev.,* 3:325-330, 1994.
Gerner E W, Meyskens F L, Jr. Polyamines and cancer: old molecules, new understanding. Nat Rev Cancer 2004; 4:781-92.
Giardiello F M, Hamilton S R, Hylind L M, Yang V W, Tamez P, Casero R A, Jr. Ornithine Decarboxylase and Polyamines in Familial Adenomatous Polyposis. Cancer Res 1997; 57:199-201.
Groves et al., *Dis. Colon Rectum,* 48:816-823, 2005.
Hanif et al., *Biochemical Pharmacology,* 52:237-245, 1996.
Hixson et al., *Cancer Epidemiol. Biomarkers Prev.,* 2:369-274, 1993.
Hubner et al., *Clin. Cancer Res.,* 14(8):2303-9, 2008.
Ignatenko et al., *Cancer Biol. Ther* 5(12):1658-64, 2006.
Japanese Pharmacopoeia, Tokyp: Society of Japanese Pharmacopoeia, 16$^{th}$ Ed., 2011.
Jasperson K W, Tuohy T M, Neklason D W, Burt R W. Hereditary and familial colon cancer. Gastroenterology 2010; 138:2044-58.
Keller J J, Giardiello F M. Chemoprevetion strategies using NSAIDs and COX-2 inhibitors. Cancer Biol Ther 2003; 2:S140-S9.
Kennedy R D, Potter D D, Moir C R, El-Youssef M. The natural history of familial adenomatous polyposis syndrome: a 24 year review of a single center experience in screening, diagnosis, and outcomes. J Pediatr Surg 2014; 49:82-6.
Kingsnorth et al., *Cancer Res.,* 43(9):4035-8, 1983.
Ladenheim et al., *Gastroenterology,* 108:1083-1087, 1995.
Lanza et al., *Arch. Intern. Med.,* 155:1371-1377, 1995.
Latchford A R, Neale K F, Spigelman A D, Phillips R K, Clark S K. Features of duodenal cancer in patients with familial adenomatous polyposis. Clin Gastroenterol Hepatol 2009; 7:659-63.
Lee, Y. S. & Dutta, A., Genes Dev 21, 1025-30, 2007.
Leonard D, Wolthuis A, D'Hoore A, et al. Different surgical strategies in the treatment of familial adenomatous polyposis: what's the role of the ileal pouch-anal anastomosis? Acta Gastroenterol Belg 2011; 74:427-34.
Lipkin, *J. Cell Biochem. Suppl.,* 28-29:144-7, 1997.
Lippman, *Nat. Clin. Pract. Oncol.,* 3(10):523, 2006.
Love et al., *J. Natl. Cancer Inst.,* 85:732-7, 1993.
Luk and Baylin, *N. Engl. J. Med.,* 311(2):80-83, 1984.
Lupulescu, *Cancer Detect. Prev.,* 20(6):634-637, 1996.
Lynch P M, Burke C A, Phillips R, et al. An international randomised trial of celecoxib versus celecoxib plus difluoromethylornithine in patients with familial adenomatous polyposis. Gut 2016; 65:286-95.
Lynch P M, Morris J S, Wen S, et al. A proposed staging system and stage-specific interventions for familial adenomatous polyposis. Gastrointest Endosc 2016; 84:115-25 e4.
Maejima et al, *Chemical Pharmacology Bulletin,* 45(3): 518-524, 1997.
Martinez et al., *Proc. Natl. Acad. Sci. USA,* 100:7859-64, 2003.
Mathus-Vliegen E M, Boparai K S, Dekker E, van Geloven N. Progression of duodenal adenomatosis in familial adenomatous polyposis: due to ageing of subjects and advances in technology. Fam Cancer 2011; 10:491-9.
McLaren et al., *Cancer Prev. Res.,* 1(7):514-21, 2008.
Meyskens F L, Jr., McLaren C E, Pelot D, et al. Difluoromethylornithine plus sulindac for the prevention of sporadic colorectal adenomas: a randomized placebo-controlled, double-blind trial. Cancer Prev Res (Phila) 2008; 1:32-8.
Meyskens et al., *J. Natl. Cancer Inst.,* 86(15):1122-1130, 1994.
Meyskens et al., *J. Natl. Cancer Inst.,* 90(16):1212-8, 1998.
Muscat et al., *Cancer,* 74:1847-1854, 1994.
Narisawa et al., *Cancer Res.,* 41(5):1954-1957, 1981.
Nigro et al., *Cancer Lett.,* (35):183-8, 1987.

Nowels et al., *Cancer. Biochem. Biophys.*, (8):257-63, 1986.
Parc Y R, Olschwang S, Desaint B, Schmitt G, Parc R G, Tiret E. Familial adenomatous polyposis: prevalence of adenomas in the ileal pouch after restorative proctocolectomy. Ann Surg 2001; 233:360-4.
Pegg, *Biochem.*, 234(2):249-262, 1986.
Physician's Desk Reference, Medical Economics Data, Montville, N.J., 1745-1747, 1999
Piazza et al., *Cancer Res.*, (55):311 3116, 1995.
Piazza et al., *Cancer Res.*, (57):2452-2459, 1997a.
Piazza et al., *Cancer Res.*, (57):2909-2915, 1997b.
Pollard and Luckert, *Cancer Res.*, 49:6471-6473, 1989.
Psaty and Potter, *N. Engl. J. Med.*, 355(9):950-2, 2006.
Rao et al., *Cancer Res.*, (55):1464-1472, 1995.
Reddy et al., *Cancer Res.*, (50):2562-2568, 1990.
Reddy et al., *Cancer Res.*, 47:5340-5346, 1987.
Roos V H, Bastiaansen B A J, Dekker E. Challenges and pitfalls of investigating duodenal cancer in patients with familial adenomatous polyposis. Gastrointest Endosc 2019; 89:355-6.
Samadder N J, Neklason D W, Boucher K M, et al. Effect of Sulindac and Erlotinib vs Placebo on Duodenal Neoplasia in Familial Adenomatous Polyposis: A Randomized Clinical Trial. JAMA 2016; 315:1266-75.
Saurin J C, Gutknecht C, Napoleon B, et al. Surveillance of duodenal adenomas in familial adenomatous polyposis reveals high cumulative risk of advanced disease. J Clin Oncol 2004; 22:493-8.
Septer S, Lawson C E, Anant S, Attard T. Familial adenomatous polyposis in pediatrics: natural history, emerging surveillance and management protocols, chemopreventive strategies, and areas of ongoing debate. Fam Cancer 2016; 15:477-85.
Serrano P E, Grant R C, Berk T C, et al. Progression and Management of Duodenal Neoplasia in Familial Adenomatous Polyposis: A Cohort Study. Ann Surg 2015; 261: 1138-44.
Simoneau et al., *Cancer Epidemiol Biomarkers Prev* 17, 292-9, 2008.
Simoneau et al., *J. Natl. Cancer Inst.*, 93:57-9, 2001.
Singh and Reddy, *Annals. NY Acad. Sci.*, (768):205-209, 1995.
Singh et al., *Carcinogenesis*, (15):1317-1323, 1994.
Sourrouille I, Lefevre J H, Shields C, et al. Surveillance of Duodenal Polyposis in Familial Adenomatous Polyposis: Should the Spigelman Score Be Modified? Dis Colon Rectum 2017; 60:1137-46.
Spigelman et al., *Lancet*, 783-785, 1989.
Steinbach G, Lynch P M, Phillips R K, et al. The effect of celecoxib, a cyclooxygenase-2 inhibitor, in familial adenomatous polyposis. N Engl J Med 2000; 342:1946-52.
Strejan et al., *Cell Immunol.*, 84(1):171-184, 1984.
Su et al., *Science*, (256):668-670, 1992.
Syngal S, Brand R E, Church J M, et al. ACG clinical guideline: Genetic testing and management of hereditary gastrointestinal cancer syndromes. Am J Gastroenterol 2015; 110:223-62.
Tajika et al., *J. Gastrointest. Surg.*, 13:1266-1273, 2009.
Tempero et al., *Cancer Res.*, 49(21):5793-7, 1989.
Thiruvengadam S S, Lopez R, O'Malley M, et al. Spigelman stage IV duodenal polyposis does not precede most duodenal cancer cases in patients with familial adenomatous polyposis. Gastrointest Endosc 2019; 89:345-54 e2.
Thomas and Thomas, *J. Cell Mol. Med.*, 7:113-26, 2003.
Thompson et al., *Cancer Res*, (45):1170-3, 1985.
Thompson et al., *J. Natl. Cancer Inst.*, (87):125-1260, 1995.
Thompson-Fawcett M W, Marcus V A, Redston M, Cohen Z, McLeod R S. Adenomatous polyps develop commonly in the ileal pouch of patients with familial adenomatous polyposis. Dis Colon Rectum 2001; 44:347-53.
United States Pharmacopeia and National Formulary (USP 39-NF 34). Rockville, Md.; 2015.
Vander Heiden, M. G. *Nat Rev Drug Discov* 10, 671-84, 2011.
Vane and Botting, *Adv Exp Med Biol.*, 433:131-8, 1997.
Wallace, *Eur. J. Clin. Invest.*, 30:1-3, 2000.
Wang et al., *Clin Cancer Res* 17, 2570-80, 2011.
Weeks et al., *Proc. Nat'l Acad. Sci. U.S.A.*, (79):6028-32, 1982.
Wu J S, McGannon E A, Church J M. Incidence of neoplastic polyps in the ileal pouch of patients with familial adenomatous polyposis after restorative proctocolectomy. Dis Colon Rectum 1998; 41:552-6.
Zell J A, Pelot D, Chen W P, McLaren C E, Gerner E W, Meyskens F L. Risk of cardiovascular events in a randomized placebo-controlled, double-blind trial of difluoromethylornithine plus sulindac for the prevention of sporadic colorectal adenomas. Cancer Prev Res (Phila) 2009; 2:209-12.
Zhang et al., *Genes Dev* 26, 461-73, 2012.

What is claimed is:

1. A method of treating a patient having familial adenomatous polyposis (FAP), the method comprising administering to the patient a pharmaceutical therapy comprising a combined effective amount of eflornithine and sulindac, wherein the patient has an at least partially intact lower gastrointestinal tract.

2. The method of claim 1, wherein the method delays or prevents a familial adenomatous polyposis (FAP) event and/or FAP progression in the patient.

3. The method of claim 1, wherein the method delays FAP disease progression in the patient.

4. The method of claim 1, wherein the method delays or prevents the need for excisional intervention.

5. The method of claim 1, wherein the method delays or prevents the development of adenomas.

6. The method of claim 5, wherein the adenomas are high risk adenomas.

7. The method of claim 1, wherein the method delays polyposis progression.

8. The method of claim 7, wherein the method delays the need for endoscopic excision or surgical resection.

9. The method of claim 1, wherein the method prevents polyposis progression.

10. The method of claim 9, wherein the method prevents the need for endoscopic excision or surgical resection.

11. The method of claim 1, wherein the method delays the formation of colorectal cancer in the patient.

12. The method of claim 1, wherein the method prevents the formation of colorectal cancer in the patient.

13. The method of claim 1, wherein the patient has a colorectum, a retained rectum, or an ileal pouch.

14. The method of claim 1, wherein the combined effective amount of eflornithine and sulindac comprises 750 mg/day eflornithine and 150 mg/day sulindac.

15. The method of claim 14, wherein the eflornithine and sulindac are administered in a single formulation.

16. The method of claim 15, wherein the single formulation comprises about 375 mg of eflornithine hydrochloride monohydrate.

17. The method of claim 15, wherein the single formulation comprises about 288.6 mg of eflornithine in its anhydrous, free base form.

18. The method of claim 15, wherein the single formulation comprises about 75 mg of sulindac.

19. The method of claim 15, wherein the single formulation is in the form of a tablet.

20. The method of claim 15, wherein the patient is administered two units of the single formulation per day.

\* \* \* \* \*